(12) United States Patent
Lee et al.

(10) Patent No.: US 10,011,589 B2
(45) Date of Patent: Jul. 3, 2018

(54) TREATMENTS FOR GASTROINTESTINAL CONDITIONS

(71) Applicants: BOARD OF REGENTS, THE UNIVERSITY OF TEXAS SYSTEM, Austin, TX (US); ST. JUDE CHILDREN'S RESEARCH HOSPITAL, INC., Memphis, TN (US)

(72) Inventors: Richard E. Lee, Cordova, TN (US); Philip T. Cherian, Memphis, TN (US); Julian G. Hurdle, Houston, TX (US); Xiaoqian Wu, Houston, TX (US)

(73) Assignees: Board of Regents, The University of Texas System, Austin, TX (US); St. Jude Children's Research Hospital, Inc., Memphis, TN (US)

( * ) Notice: Subject to any disclaimer, the term of this patent is extended or adjusted under 35 U.S.C. 154(b) by 0 days.

(21) Appl. No.: 15/125,451

(22) PCT Filed: Mar. 12, 2015

(86) PCT No.: PCT/US2015/020224
§ 371 (c)(1),
(2) Date: Sep. 12, 2016

(87) PCT Pub. No.: WO2015/138753
PCT Pub. Date: Sep. 17, 2015

(65) Prior Publication Data
US 2017/0073332 A1    Mar. 16, 2017

Related U.S. Application Data

(60) Provisional application No. 61/951,878, filed on Mar. 12, 2014.

(51) Int. Cl.
*C07D 403/14* (2006.01)
*C07D 403/12* (2006.01)
*C07D 403/06* (2006.01)

(52) U.S. Cl.
CPC ......... *C07D 403/14* (2013.01); *C07D 403/06* (2013.01); *C07D 403/12* (2013.01)

(58) Field of Classification Search
CPC ... C07D 403/14; C07D 403/06; C07D 403/12
USPC ....................................................... 514/402
See application file for complete search history.

(56) References Cited

U.S. PATENT DOCUMENTS

2010/0317707 A1    12/2010    Ren et al.

OTHER PUBLICATIONS

Hurdle, JG et al. Reutericydin and related analogues kill stationary phase Clostridium difficile at achievable colonic concentrations. Journal of Antimicrobial Chemotherapy vol. 66, 2011, pp. 1773-1776, published Online May 31, 2011 (online), [retrieved on May 11, 2015). Retrieved from the Internet <URL: http://jac.oxfordjournals.org/contenV66/8/1773  full.pdf+htmf><doi: 10.1093/jac/dkr201>; p. 1773, col. 1, paragraph 1; p. 1773, col. 2, paragraph 1; p. 1774, table 1.

Matiadis, D et al. Design and Synthesis of Optically Active Esters of gamma-Amino-beta-oxo Acids as Precursors for the Synthesis of Tetramic Acids Derived from L-Serine, L Tyrosine, and L-Threonine. European Journal of Organic Chemistry, vol. 2010, No. 31, Nov. 2010, pp. 5989-5995.

Katzka, CP. Synthesis of Tetramic Acids and Investigation of their Biological Properties Jun. 29, 2006, pp. 1-151 (online), [retrieved on May 11, 2015). Retrieved from the Internet <URL: https://www.deutsche-digitale-bibliothek.de/binary/Q62QXIEPQEAVDZOSIK05CEQS6W4LVJB P/fufl/1 . pdf>; p. 75, paragraph 3; p. 76, table 7.

Ueda, C et al. Anti-Clostridium difficile Potential of Tetramic Acid Derivatives from Pseudomonas aeruginosa Quorum-Sensing Autoinducers. Antimiacobial Agents and Chemotherapy, vol. 54, No. 2, Feb. 2010. pp. 683-688 [online], [retrieved on May 11, 2015). Retrieved from the Internet <URL: http://aac.asm.org/contenU54/2/683.full.pdf+html><doi: 10.1128/AAC.00702-09>; entire publication.

Bersani, et al., "PEG-metronidazole conjugates: synthesis, in vitro and in vivo properties", Il Farmaco, 60(9), 2005, 783-788, XP02769601.

Extended Search Report issued in European Application No. 157621251, dated Jul. 11, 2017.

*Primary Examiner* — Kristin A Vajda
(74) *Attorney, Agent, or Firm* — Meunier Carlin & Curfman LLC

(57) ABSTRACT

Compounds for the treatment of bacterial and parasitic infections which are hybrid compounds of compounds having antibacterial or antiparasitic activity and compounds that decrease the absorption of the hybrid compound from the gastrointestinal tract. The compounds are preferably for use against *C. difficile* infections and comprise a hybrid molecule of an anti-*C. difficile* compound such as a nitroimidazole and a tetramic acid derivative.

12 Claims, 14 Drawing Sheets

| Compound | Structure | MIC (mg/L) | |
|---|---|---|---|
| | | R20291 | BAA-1875 |
| metronidazole | | 0.125 | 0.25 |
| vancomycin | | 2 | 0.75 |
| 1971 | 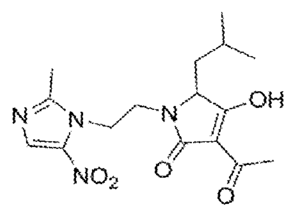 | 1 | 2 |
| 2122 | 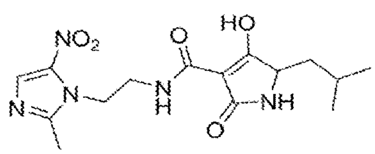 | 24 | 32 |
| 2123 | 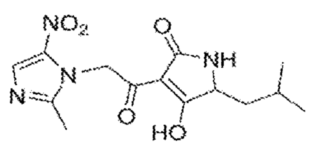 | 12 | 20 |

FIGURE 8

| Compound | Structure | MIC (mg/L) | |
|---|---|---|---|
| | | R20291 | BAA-1875 |
| 2153 | H- | >64 | >64 |
| 2158 | $CH_3$- | 4 | 8 |
| 2156 | (isobutyl) | 1 | 2 |
| 2155 | (sec-butyl) | 0.25 | 1 |
| 2157 | (CH2CH2SCH3) | 8 | 16 |
| 2154 | (benzyl) | 4 | 4 |
| 2171 | (4-OtBu-benzyl) | 0.5 | 2 |
| 2172 | (4-OH-benzyl) | >64 | >64 |
| 2345 | (4-phenylbenzyl) | 0.5 | 0.25 |
| 2313 | (CH2-S-CH2-Ph) | 2 | 1.5 |
| 2173 | (CH(CH3)-OtBu) | 1 | 2 |
| 2174 | (CH(CH3)-OH) | >64 | >64 |
| 2124 | (CH2-OtBu) | 2 | 3 |
| 2125 | (CH2-OH) | >64 | >64 |
| 2175 | (CH2CH2-COOtBu) | 2 | 4 |

FIGURE 9A

| Compound | Structure | MIC (mg/L) | |
|---|---|---|---|
| 2176 | COOH | >64 | >64 |
| 2177 | COOtBu | 8 | 16 |
| 2178 | COOH | >64 | >64 |
| 2179 | NHBoc | 8 | 16 |
| 2180 | NH$_2$ | >64 | >64 |
| 2309 | indole-NBoc | 1.5 | 0.75 |
| 2310 | indole-NH | 6 | 16 |
| 2490 | N-methylindole | 1 | 1.5 |
| 2344 | naphthyl | 1 | 1 |
| 2312 | imidazole-NH | >64 | >64 |
| 2489 | N-methylimidazole | >64 | >64 |

FIGURE 9B

| Name | MIC mg/L) BAA-1803 |
|---|---|
| Metronidazole | 0.25 |
| 1941 | 16 |
| 1971 | 1 |
| 2122 | 24 |
| 2123 | 12 |
| 2124 | 2 |
| 2125 | >64 |
| 2153 | 64 |
| 2154 | 4 |
| 2155 | 1 |
| 2156 | 2 |
| 2157 | 8 |
| 2158 | 16 |
| 2171 | 2 |
| 2172 | >64 |
| 2173 | 2 |
| 2174 | >64 |
| 2175 | 4 |
| 2176 | >64 |
| 2177 | 8 |
| 2178 | >64 |
| 2179 | 16 |
| 2180 | >64 |
| 2309 | 0.5 |
| 2310 | 16 |
| 2311 | 0.5 |
| 2312 | >64 |
| 2313 | 2 |
| 2314 | 16 |
| 2315 | 1 |
| 2344 | 1 |
| 2345 | 0.5 |
| 2489 | >64 |
| 2490 | 1 |
| 2699 | >128 |
| 2700 | >128 |

FIGURE 10

| Compound | Structure | MIC (mg/L) | |
|---|---|---|---|
| | | R20291 | BAA-1875 |
| metronidazole | 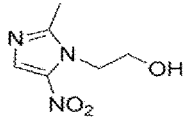 | 0.125 | 0.5 |
| 2698 (des-nitro metronidazole) | 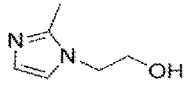 | >128 | >128 |
| 2344 | 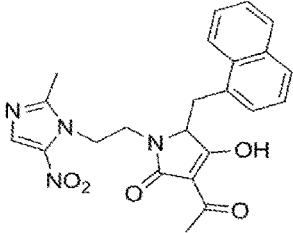 | 1 | 1 |
| 2699 | 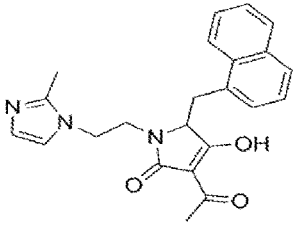 | >128 | >128 |
| 2345 | 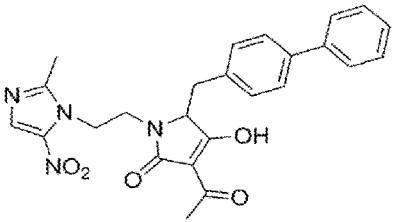 | 0.5 | 0.25 |
| 2700 | 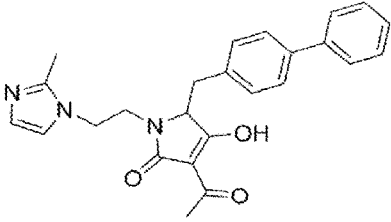 | >128 | >128 |
FIGURE 11

| Strain | Mean MIC (mg/L) | | | | | |
|---|---|---|---|---|---|---|
| | 1971 | 2344 | 2345 | 2490 | metronidazole | vancomycin |
| CD32 | 0.5 | 0.375 | 0.25 | 0.75 | 0.19 | 1.5 |
| CD40 | 2 | 1 | 1.5 | 3 | 0.5 | 1.5 |
| CD42 | 0.5 | 0.25 | 0.25 | 0.75 | 0.12 | 0.75 |
| CD101 | 1.25 | 0.375 | 0.31 | 0.75 | 0.25 | 0.375 |
| CD196 | 1.5 | 0.75 | 0.625 | 2 | 0.5 | 0.75 |
| CD222 | 0.5 | 0.5 | 0.25 | 0.75 | 0.25 | 1.5 |
| CD233 | 0.5 | 0.25 | 0.175 | 0.625 | 0.175 | 1 |
| CD630 | 1.25 | 0.625 | 0.375 | 1.5 | 0.375 | 1 |
| CD1385 | 0.75 | 0.25 | 0.175 | 0.75 | 0.25 | 1.5 |
| CD1742 | 0.19 | 0.25 | 0.12 | 0.625 | 0.12 | 0.625 |
| CD1769 | 1 | 0.5 | 0.375 | 1.5 | 0.375 | 0.5 |
| CD1824 | 1.5 | 0.75 | 0.625 | 2 | 0.5 | 2 |
| CD1854 | 0.75 | 0.375 | 0.19 | 1 | 0.25 | 0.75 |
| BAA-1803 | 1 | 0.5 | 0.5 | 1 | 0.5 | 2 |
| BAA-1875 | 0.75 | 0.5 | 0.375 | 1.5 | 0.25 | 0.5 |
| CF5 | 1.5 | 0.75 | 1 | 2 | 0.5 | 1 |
| Liv22 | 2 | 1 | 0.5 | 2 | 0.75 | 2 |
| R20291 | 1 | 0.75 | 0.5 | 2 | 0.5 | 0.75 |
| UK-1 | 0.75 | 0.31 | 0.31 | 1 | 0.175 | 0.5 |
| VPI 10463 | 1.25 | 0.375 | 0.31 | 0.625 | 0.175 | 1.5 |
| [a]MIC Range | 0.12-2 | 0.12-1 | 0.12-2 | 0.25-4 | 0.12-0.5 | 0.25-2 |
| Mean MIC$_{50}$ | 1 | 0.5 | 0.31 | 1 | 0.25 | 1 |
| Mean MIC$_{90}$ | 1.5 | 0.75 | 0.625 | 2 | 0.5 | 2 |

[a]range is based on accrual values.

FIGURE 12

| Bacteria | Strain | Mean MIC (mg/L) | | | | | |
|---|---|---|---|---|---|---|---|
| | | 1971 | 2344 | 2345 | 2490 | metronidazole | vancomycin |
| *Actinomycetes viscosus* | HM238 | 64 | 128 | 32 | 256 | 32 | 0.5 |
| *Bacteroides eggerthii* | HM210 | 0.5 | 0.5 | 1 | 1 | 0.25 | 24 |
| *Bacteroides fragilis* | ATCC25285 | 128 | 96 | 24 | 256 | >512 | 2 |
| *Bacteroides fragilis* | HM20 | 0.5 | 0.25 | 1 | 1.5 | 0.25 | 16 |
| *Bacteroides ovatus* | ATCC8483 | 3 | 1.5 | 1 | 2 | 0.75 | 64 |
| *Bacteroides ovatus* | HM222 | 2 | 1.25 | 0.375 | 2 | 0.75 | 24 |
| *Bacteroides sp.* | HM18 | 0.5 | 0.5 | 1 | 1.5 | 0.5 | 96 |
| *Bacteroides sp.* | HM19 | 2 | 1.5 | 2 | 6 | 0.375 | 128 |
| *Bacteroides sp.* | HM23 | 1 | 1 | 1.25 | 2 | 0.375 | 96 |
| *Bacteroides sp.* | HM28 | 1.5 | 0.75 | 1.5 | 2 | 0.75 | 48 |
| *Bifidobacterium breve* | HM421 | >512 | 256 | 64 | 384 | >512 | 0.5 |
| *Bifidobacterium sp.* | HM30 | 512 | 192 | 48 | 192 | >512 | 0.5 |
| *Fusobacterium nucleatum* | HM260 | 1 | 4 | 10 | 4 | 0.25 | >512 |
| *Fusobacterium periodonticum* | HM41 | 0.5 | 0.5 | 1.5 | 1.5 | <0.06 | 192 |
| *Lactobacillus johnsonii* | HM643 | >512 | >512 | 192 | >512 | >512 | 6 |
| *Porphyromonas uenonis* | HM130 | 48 | 16 | 4 | 48 | 384 | 3 |

FIGURE 13

| Compound | Cytotoxicity, $IC_{50}$ (mg/L) | Compound | Cytotoxicity, $IC_{50}$ (mg/L) |
|---|---|---|---|
| metronidazole | 147.34 | 2174 | 130.7 |
| vancomycin | ND | 2124 | 133.8 |
| 1971 | 138.7 | 2125 | 127.5 |
| 2122 | 134.1 | 2175 | 140.8 |
| 2123 | 131.8 | 2176 | 129.7 |
| 2153 | 140.5 | 2177 | 133.0 |
| 2158 | 140.3 | 2178 | 83.19 |
| 2156 | 133.5 | 2179 | 136.3 |
| 2155 | 141.3 | 2180 | 125.4 |
| 2157 | 139.6 | 2309 | 120.7 |
| 2154 | 139.9 | 2310 | 169.2 |
| 2171 | 173.5 | 2490 | 111.6 |
| 2172 | 133.8 | 2344 | 133.2 |
| 2345 | ND | 2312 | 138.2 |
| 2313 | 151.1 | 2489 | 140.7 |
| 2173 | 135.4 | | |

FIGURE 14

| Compound | $P_{app}$ (nm/s) | | Efflux Ratio |
| --- | --- | --- | --- |
| | A-B | B-A | |
| 1971 | 195.3 ± 103.9 | 230.8 ± 34.7 | 1.2 |
| 2124 | 271.5 ± 10.4 | 249.8 ± 23.4 | 0.9 |
| 2154 | 307 ± 35.6 | 215.4 ± 21.1 | 0.7 |
| 2155 | 294.3 ± 41.5 | 202.2 ± 9.5 | 0.7 |
| 2156 | 273.8 ± 2.1 | 208.3 ± 8.4 | 0.8 |
| 2173 | 214.9 ± 10.4 | 221.1 ± 18.7 | 1 |
| 2309 | 176.9 ± 14.3 | 171.6 ± 2.5 | 1 |
| 2313 | 284.5 ± 34.7 | 208.1 ± 8.8 | 0.7 |
| 2315 | 292.9 ± 32.1 | 276 ± 12.5 | 0.9 |
| 2344 | 246.3 ± 21 | 227.7 ± 85.7 | 0.9 |
| 2345 | 191.5 ± 56.9 | 244.3 ± 16.4 | 1.3 |
| 2490 | 358.51 ± 12 | 234.84 ± 10.8 | 0.7 |
| metronidazole | 480.1 ± 54.8 | 363.2 ± 30.6 | 0.8 |
| Vancomycin | 214.8 ± 2.7 | 141.7 ± 22.8 | 0.7 |

FIGURE 15

TREATMENTS FOR GASTROINTESTINAL CONDITIONS

CROSS REFERENCE TO RELATED APPLICATION

This application is a U.S. National Stage of International Patent Application Ser. No. PCT/US2015/20224, filed Mar. 12, 2015 entitled "TREATMENTS FOR GASTROINTESTINAL CONDITIONS", which claims priority to U.S. Provisional Patent Application Ser. No. 61/951,878, filed on Mar. 12, 2014. The disclosures of the above-identified co-pending applications are incorporated herein by reference in their entirety.

STATEMENT REGARDING FEDERALLY SPONSORED RESEARCH OR DEVELOPMENT

This invention was made with government support under NIH grant 5R01AT006732. The government has certain rights in the invention.

BACKGROUND OF THE INVENTION

Throughout the world, gastrointestinal (GI) infections are a major cause of morbidity and mortality in humans. Etiologic agents include a range of aerobic and anaerobic bacterial and parasitic species. A leading treatment for these infections is the nitroimidazole drug metronidazole that is marketed as Flagyl® and is either used alone or in combination with other therapeutic drugs. Metronidazole has been in clinical use for more than 50 years.

One of the principal infections treated by metronidazole is mild-to-moderate *Clostridium difficile* infection (CDI). CDI is the leading cause of antibiotic-associated diarrhea in hospitals and is now a major public health problem in developed countries such as the United States and Europe.

Metronidazole benefits from being potent against *C. difficile*, demonstrating bactericidal properties, but is primarily for mild to moderate cases of CDI. The key issue with the use of metronidazole in more severe cases of CDI is that it is highly absorbed from the gastrointestinal tract. Metronidazole is so highly absorbed (>80% in 1-2 h) from the gastrointestinal tract that only low concentrations of the drug occur at the site of infection in the gastrointestinal tract. In cases of severe CDI more than 25% of patients typically relapse following metronidazole therapy.

Other gastrointestinal diseases that are treated with metronidazole may also experience sub-optimal treatment due to the low gastrointestinal concentration of the drug. These diseases include but are not limited to anaerobic bacterial and parasitic infections such as Amebiasis, Giardiasis, infections from *Helicobacter pylori* and *Gardnerella*, and Crohn's and other inflammatory bowel diseases.

It would be advantageous for the treatment of gastrointestinal infections and conditions to be able to administer a drug that has excellent effectiveness that also remains in the GI tract for a long time period. In particular, it would be beneficial for the treatment of CDI and other gastrointestinal infections and conditions to have a drug that has excellent anti-bacterial effectiveness that also remains in the GI tract for a long time period. For example, it would be advantageous to provide a drug having the anti-bacterial activity of metronidazole, but which is not readily absorbed from the GI tract.

Low or non-absorbed compounds bearing a nitroimidazole group, such as metronidazole, could represent a more efficacious treatment approach for CDI and other gastrointestinal conditions. The ability to achieve high local concentrations could also lower the prospects for resistance to emerge and, by lowering systemic exposure, prevent or reduce common known side effects associated with metronidazole and other nitroimidazoles.

SUMMARY OF THE INVENTION

In one aspect the invention provides methods and compounds for treating gastrointestinal conditions, such as bacterial infections caused by the organism *C. difficile*. The compounds are hybrid compounds of compounds having the desired activity and compounds that decrease the absorption of the hybrid compound from the gastrointestinal tract. The methods comprise administering compounds that are hybrid compounds of compounds having the desired activity and compounds that decrease the absorption of the hybrid compound from the gastrointestinal tract. Preferred embodiments employ nitroimidazole compounds having activity against *C. difficile* and tetramic acid derivatives, which provide reduced absorption.

In another aspect the invention provides compounds and methods for treating conditions that are typically treated with nitroimidazoles and wherein decreased absorption would provide enhanced benefit. Conditions include GI conditions such as bacterial infections caused by the organism *C. difficile, Helicobacter pylori*, or *Gardnerella*, parasitic infections such as Amebiasis, Giardiasis, and also Crohn's and other inflammatory bowel diseases. Other conditions include periodontitis and oral infections caused by anaerobes, for which metronidazole is known to be used in patients where mechanical debridement is not possible or successful.

The present invention further provides a method for increasing the effectiveness of a compound in the treatment of a GI condition by hybridizing the compound with another compound that decreases the absorption of the hybrid compound from the GI tract.

Besides achieving superior efficacy in treating diseases compared to metronidazole, the present invention also provides compounds with lower toxicity than nitroimidazoles, because they are non-absorbed or less absorbed from the gastrointestinal tract, thus preventing or lowering systemic exposure.

Nitroimidazole drugs, including metronidazole, ornidazole, and nimorazole are potent against anaerobic bacteria and parasites, but are highly absorbed from the GI tract. A good drug against gastrointestinal infections should be non-absorbed or have low absorption (<20%). The invention provides nitroimidazole drugs that are relatively non-absorbed or low-absorbed. These compounds contain the core portion of the nitroimidazole combined with a tetramic acid derivative. The addition of the tetramic acid derivative decreases absorption of the nitroimidazole in the GI tract.

Suitable absorption decreasing compounds are tetramic acids, thus the present invention provides a method of localizing drugs for diverse disease indications to the gastrointestinal tract by conjugating these to a tetramic acid, substituted tetramic acid, or chemical group that has similar chemical properties to the tetramic acid core with or without substituents, and corresponding tautomers (collectively referred to herein as a "tetramic acid derivative").

A series of hybrid compounds having a nitroimidazole group and a tetramic acid group were synthesized and evaluated in terms of anti *C. difficile* activity, gastric permeability, in vivo pharmacokinetics, efficacy in the hamster model of CDI, and mode of action. Most compounds were less absorbed than metronidazole in in vitro permeability assays, with preferred compounds compartmentalizing in the colon rather than the bloodstream of animals; they were at least an order less absorbed than metronidazole. Four compounds having diverse structures and representing a wide array of structures were tested and were more efficacious (p<0.05) than metronidazole in *C. difficile* infected animals. Improved efficacy was not due to an alternate mode of action, as the compounds retained the mode of action of metronidazole, relying on biochemical reduction of the nitro-group to impose cellular stress and DNA damage.

In another aspect, the hybrid molecules are useful in treating parasitic GI infections. Furthermore, in addition to gastrointestinal diseases that are treated with nitroimidazoles, other conditions that are treated with nitroimidazoles might benefit from application of the present invention.

The term "gastrointestinal tract" as used herein refers to all structures between the lips and the anus, and includes the mouth, tongue, esophagus, stomach, small intestine, large intestine, rectum, and anus.

BRIEF DESCRIPTION OF THE DRAWINGS

FIG. 8 illustrates the structures of exemplary nitroimidazole-tetramic acid hybrid molecules and their minimum inhibitory concentrations (MICs) for two *C. difficile* strains R20291 and BAA-1875.

FIGS. 9A and 9B illustrate the structures of nitroimidazole-tetramic acid hybrid molecules designed via structure-activity relationship (SAR) studies based on the 1971 compound, their MICs for two *C. difficile* strains R20291 and BAA-1875, and their cytotoxicity.

FIG. 10 shows the in vitro activities (MICs) of compounds against the *C. difficile* strain BAA-1803.

FIG. 11 illustrates the structures of certain nitroimidazole-tetramic acid hybrid molecules and is a comparison of mechanism of action of nitro and des-nitro metronidazole and analogs.

FIG. 12 shows that the in vitro activities of representative compounds 1971, 2344, 2345, and 2490 against a panel of 20 *C. difficile* strains is similar to metronidazole.

FIG. 13 illustrates that the in vitro activities of representative compounds 1971, 2344, 2345, and 2490 against a panel of gastrointestinal flora is similar to metronidazole.

FIG. 14 provides cytotoxicity data of certain compounds.

FIG. 15 illustrates results of a Caco-2 cell intestinal permeability assay.

DETAILED DESCRIPTION OF THE INVENTION

Figure 1:
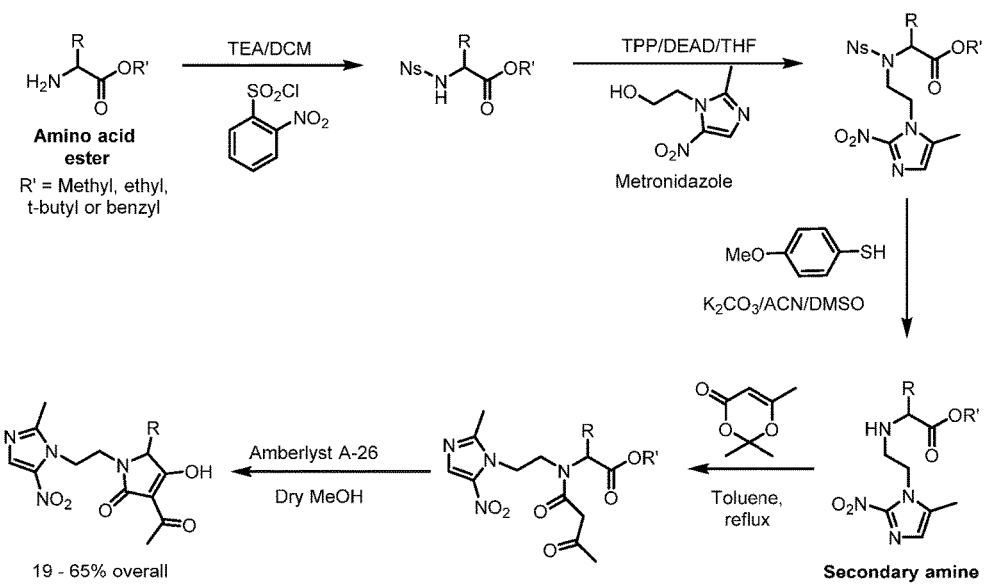
FIG. 1 illustrates a synthetic method used to make nitroimidazole-tetramic acid hybrid molecules wherein the nitroimidazole is linked to the 1N-position of the tetramic acid derivative.

Metronidazole (MTZ) is active against *C. difficile* but is highly absorbed (>80%) in the gastrointestinal tract and thus is not suitable for treating severe infections caused by *C. difficile*. This limitation is overcome by hybridizing metronidazole to tetramic acid, thus allowing it to be retained in the GI tract and providing a more efficacious approach to treating *C. difficile* infections.

While the description here is directed primarily to metronidazole and tetramic acid hybrids, it should be understood that the present invention also applies to other hybrid molecules with similar chemical properties. The important elements are a molecule that has relevant activity and a molecule that decreases GI tract absorption of the hybrid molecule.

The active molecule is desirably an anti-infective, preferably an anti-bacterial or anti-parasitic molecule. In preferred embodiments, the active molecule is a nitroimidazole, including tinidazole, nimorazole, dimetridazole, 6-Amino PA824, ornidazole, megazol, azanidazole, benznidazole, pimonidazole, and metronidazole.

The absorption decreasing molecule desirably decreases the GI absorption of the hybrid molecule by at least 50% over the GI absorption of the active agent alone. In preferred embodiments, the absorption decreasing molecule is a tetramic acid derivative.

In addition, while the description is primarily directed to treatment of *Clostridium difficile* infection (CDI), it should be understood that the molecules are also suitable for treatment of other conditions which are treated with nitroimidazoles and which would be more effective if their GI tract absorption was decreased.

Other relevant gastrointestinal conditions include gastrointestinal infections caused by bacteria including, but not limited to, *Clostridium perfringens* and other *Clostridia* species, *Helicobacter pylori*, *Bacteroides* species, and gastrointestinal infections caused by parasitic species including *Entamoeba* species, *Enterobius* species, *Strongyloides* species, *Giardia* species, *Ancylostoma* species, and *Necator* species. In addition the molecules might be effective for treatment of Crohn's and other inflammatory bowel diseases that are treated with nitroimidazoles. Further, the hybrid molecules and methods might be useful for treating periodontitis and oral infections caused by anaerobes or associated bacteria, for which metronidazole is used in patients where mechanical debridement is not possible or successful.

The hybrid molecules should be effective against all infections due to bacteria or protozoans that are treated by metronidazole and other nitroimidazole drugs. It should be understood that demonstration of efficacy in the disease setting of CDI and demonstration that exemplary molecules retain the mechanism of action of metronidazole, indicates that the compounds can be used in the same indications as metronidazole and other nitroimidazoles but achieve superior therapeutic outcomes.

The hybrid molecules are made by modifying the N1 and C3 positions of the tetramic acid core. FIGS. 1 through 7 show synthesis pathways for the hybrid molecules. Three basic analogs are shown in FIG. 8, 1971 in which metronidazole is linked to the N1-position of tetramic acid, 2122 in which metronidazole is linked to the C3-position of the tetramic acid via a carboxamide, and 2123 in which metronidazole and tetramic acid are linked via a carboxyl group.

MIC testing (the results are shown in FIG. 8) revealed that metronidazole linked to tetramic acid at the N1-position, as in 1971 (MIC=1-2 µg/mL), was optimal for producing molecules that retain activity against *C. difficile;* 2122 and 2123 were 24-fold and 10-fold less active than 1971. Although 1971 was 4 to 8 fold less active than metronidazole (MIC=0.25 µg/mL), this did not diminish expansion of a series of compounds based on 1971, since lower activity could be compensated for in vivo, by increased local concentration of drug.

Accordingly, in one embodiment, the compound of the invention is a nitroimidazole-tetramic acid hybrid molecule in which the nitroimidazole is linked to the 1N-position of the tetramic acid and has the formula shown below as Formula I:

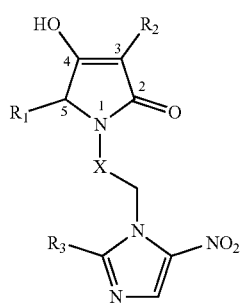

Formula I

Wherein:
A) X is —CH$_2$—, —CH$_2$CH$_2$—, or —CO;
B) R1 is
  i) a straight alkyl chain of one to six carbons, such as methyl, ethyl, n-propyl, n-pentyl, or n-hexyl or branched alkyl chain of one to six carbons,
  ii) a branched alkyl chain of three to six carbons, such as iso-propyl, iso-butyl, sec-butyl, tert-butyl or isopentyl,
  iii) a straight or branched alkyl of chain of one to four carbons containing a protected polar functional group such as hydroxyl, carboxylic acid, amine or thiol, wherein examples of protecting groups are tert-butyl, benzyl, tert-butyl carbamate and trityl,
  iv) a saturated or unsaturated (monocyclic or bicyclic) ring system of 3 to 16 carbons such as cyclopropyl, cyclobutyl, cyclopentyl, cyclobutyl methyl, cyclopentyl methyl, 1-napthyl, 2-napthyl wherein the ring systems may or may not be substituted, which substituents may be for example, chloro, fluoro, bromo, or methoxy,
  v) an aryl or aryl alkyl ring system such as phenyl or benzyl, or substituted phenyl or benzyl, wherein examples of substituents are chloro, fluoro, bromo, hydroxyl, methyl, ethyl, methoxy, trifluoromethoxy, morpholinyl, phenyl and piperazinyl, or
  vi) an aryl, biaryl, heteroaryl, or bihetero aryl ring system such as benzyl, substituted benzyl, biphenyl, imidazolyl, pyrrolyl, pyradinyl, pyrazinyl, indolyl, furanyl, thienyl, imidazoyl methyl, pyrrolyl methyl, pyridinyl methyl, pyrazinyl methyl, furanyl methyl, indolyl methyl and thienyl methyl, which ring systems may or may not be substituted, which substituents may be for example, chloro, fluoro, bromo, hydroxyl, or methoxy or the substituent may be a protecting group such as a tert-butyl carbamate, benzyl carbamate or trityl;
C) R2 is hydrogen or an acyl moiety that may be
  i) a C2-C8 alkyl, such as acetyl, propionyl, butanoyl, etc.
  ii) an aryl ring, such as benzoyl, where the ring may be substituted, wherein examples of substituents may be chloro, fluoro, bromo, hydroxyl, methyl, ethyl, trifluoromethoxy, and methoxy, or
  iii) a heteroaryl or substituted heteroaryl ring system, containing groups such as furanoyl, imidazoyl, pyrrodyl, or indaloyl, which may contain substituents such as chloro, fluoro, bromo, hydroxyl, methyl, ethyl, and methoxy; and
D) R3 is
  i) a hydrogen,
  ii) a straight alkyl chain of one to three carbons, such as methyl, ethyl, n-propyl, or
  iii) a branched alkyl chain of three to six carbons, such as iso-propyl, iso-butyl, sec-butyl, tert-butyl or isopentyl, In another embodiment, the compound of the invention is a nitroimidazole-tetramic acid hybrid molecule in which the nitroimidazole is attached to the 3-position of the tetramic acid and has the formula shown below as Formula II:

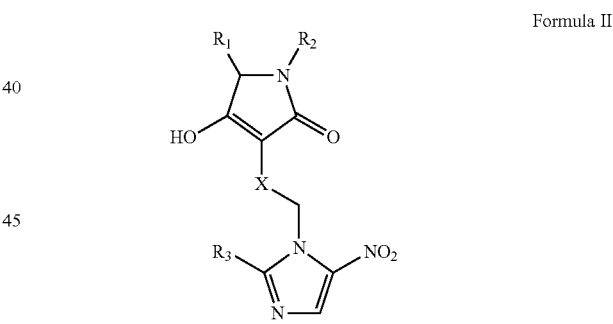

Formula II

Wherein
A) X is —CONH— or —CO;
B) R1 is
  i) a straight alkyl chain of one to six carbons, such as methyl, ethyl, n-propyl, n-pentyl, or n-hexyl or branched alkyl chain of one to six carbons,
  ii) a branched alkyl chain of three to six carbons, such as iso-propyl, iso-butyl, sec-butyl, tert-butyl or isopentyl,
  iii) a straight or branched alkyl of chain of one to four carbons containing a protected polar functional group such as hydroxyl, carboxylic acid, amine or thiol, wherein examples of protecting groups are tert-butyl, benzyl, tert-butyl carbamate and trityl,
  iv) a saturated or unsaturated (monocyclic or bicyclic) ring system of 3 to 16 carbons such as cyclopropyl, cyclobutyl, cyclopentyl, cyclobutyl methyl, cyclopentyl methyl, 1-napthyl, 2-napthyl wherein the ring systems may or may not be substituted, which substituents may be for example, chloro, fluoro, bromo, or methoxy, v) an aryl or aryl alkyl ring system such as phenyl or benzyl, or substituted phenyl or benzyl, wherein examples of substituents are chloro, fluoro, bromo, hydroxyl, methyl, ethyl, methoxy, trifluoromethoxy, morpholinyl, phenyl and piperazinyl, or vi) an aryl, biaryl, heteroaryl, or bihetero aryl ring system such as benzyl, substituted benzyl, biphenyl, imidazolyl, pyrrolyl, pyradinyl, pyrazinyl, indolyl, furanyl, thienyl, imidazoyl methyl, pyrrolyl methyl, pyridinyl methyl, pyrazinyl methyl, furanyl methyl, indolyl methyl and thienyl methyl, which ring systems may or may not be substituted, which substituents may be for example, chloro, fluoro, bromo, hydroxyl, or methoxy or the substituent may be a protecting group such as a tert-butyl carbamate, benzyl carbamate or trityl;

C) R2 is
  i) hydrogen,
  ii) a straight alkyl chain of one to three carbons, such as methyl, ethyl, n-propyl, or
  iii) a branched alkyl chain of three to six carbons, such as iso-propyl, iso-butyl, sec-butyl, tert-butyl or isopentyl; and D) R3 is
  i) hydrogen,
  ii) a straight alkyl chain of one to three carbons, such as methyl, ethyl, n-propyl,
  iii) a branched alkyl chain of three to six carbons, such as iso-propyl, iso-butyl, sec-butyl, tert-butyl or isopentyl, or
  iv) an aryl or aryl alkyl ring system such as phenyl or benzyl, or substituted phenyl or benzyl, wherein examples of substituents are chloro, fluoro, bromo, hydroxyl, methyl, ethyl, methoxy, trifluoromethoxy, morpholinyl, phenyl and piperazinyl.

Expansion of the 1971 compound series was achieved through structure-activity relationship (SAR) studies. Various amino acid R-group functionalities were employed to cover a range of physicochemical properties, such as hydrophobicity, polarity, and charge, which could also influence absorption from the intestinal tract. This led to the generation of a library of compounds with a variety of functional groups at the 5-position. FIGS. 9A and 9B show the structures of studied compounds as well as their MICs against two *C. difficile* strains. Substitution at the 5-position was important for activity as derivatives lacking a 5-substituent (2153, R=H) were >64 fold less active than parent 1971. Furthermore, hydrophobic substituents were preferred, as polar and charged substituents led to significant loss of activity. This is seen by comparing the activities of protected/deprotected pairs of aliphatic alcohols—2171/72, 2173/74 and 2124/25, carboxylic acids—2175/76 and 2177/78 and amines—2179/80, 2309/10 and 2311/12. The lack of activity of these polar analogs is most likely due to poor membrane partition, resulting in low intracellular levels. In the case of the hydrophobic substituents, both aliphatic and aromatic groups were tolerated and their activities were generally comparable to 1971 (FIGS. 9A and 9B). Thus, the SAR study provided several active analogs in addition to 1971 and these were used in further analysis.

At the 3-position, lack of an acyl substituent (2314) led to loss of activity (FIG. 10). No difference in MIC was observed between an acetyl substituent (1971) and a 4-fluorobenzoyl substituent (2315) at 3-position (FIG. 10) suggesting that the 3-position can accommodate substituents of varying sizes and shapes similar to the 5-position. This may be useful for further improvements to the physicochemical properties of the compounds.

The hybrid compounds can be synthesized by a variety of mechanisms. Complete details are provided in the examples. In one embodiment, for synthesis of metronidazole-tetramic acid hybrid molecules wherein the metronidazole is linked to the 1N-position of the tetramic acid, the alcohol of metronidazole was displaced by nosylated amino acid esters using the Fukuyama-Mitsunobu amination protocol. Following removal of the nosyl group, the free secondary amine was acylated with a ketene-acetone adduct and the obtained intermediate was cyclized under Lacey-Dieckmann conditions. The final mixtures were purified by reverse phase column chromatography (RPCC) to provide the desired metronidazole-tetramic acid hybrids in 19-65% overall yields.

For synthesis of a metronidazole-tetramic acid hybrid molecule in which the metronidazole is attached to the 3-position of the tetramic acid and where X is —CONH—, the alcohol of metronidazole was converted to the amine under Mitsunobu conditions and the 3-methoxycarbonyl tetramic acid was synthesized from Leu-OMe hydrochloric acid and methyl malonyl chloride using Lacey-Dieckmann conditions. Reaction of these two intermediates in microwave at 100° C. for 10 min followed by purification by RPCC provided the hybrid product. For another product, the alcohol of metronidazole was oxidized to acid by Jones oxidation and the tetramic acid was synthesized from Z-Leu-OH and (Triphenylphosphoranylidene)ketene. Finally, the two intermediates were coupled in presence of EDC/DMAP and purified by RPCC to provide the hybrid product. All reported compounds were at least 95% pure.

The Caco-2 cell permeability assay provides good prediction of compound intestinal absorption and was used to test the compounds. All hybrid compounds tested showed poorer (compared to metronidazole) permeation from the apical to the basolateral side of the cells, indicating that they are likely to be compartmentalized in the lumen of the GI tract.

Pharmacokinetic studies in hamsters were carried out to test hybrid compounds and also revealed that the hybrid compounds had better retention in the GI tract than metronidazole.

Pharmaceutical compositions can be prepared from the hybrid compounds in combination with other active agents, if desired, and one or more inactive ingredients such as pharmaceutically acceptable carriers as set forth below.

The pharmaceutical compositions may be employed in powder or crystalline form, in liquid solution, or in suspension. The compositions are desirably administered orally.

Oral formulations may take such forms as tablets, capsules, oral suspensions and oral solutions. The oral compositions may utilize carriers such as conventional formulation agents, and may include sustained release properties as well as rapid delivery forms. The dosage to be administered depends to a large extent on a variety of factors, including the condition, size and age of the subject being treated, the route and frequency of administration, and the renal and hepatic function of the subject. An ordinarily skilled physician can readily determine and prescribe the effective amount required.

Determination of a therapeutically effective amount may be readily made by the clinician, as one skilled in the art, by the use of known techniques and by observing results obtained under analogous circumstances. The dosages may be varied depending upon the requirements of the patient in the judgment of the attending clinician and the severity of the condition being treated.

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric.

EXAMPLES

All reagents and solvents were purchased from commercial sources and were used without further purification. The final reaction mixtures were purified by reverse phase flash chromatography using a Biotage Isolera Flash Purification System. The yields quoted are unoptimized. The purity and mass spectra of the synthesized compounds were determined on a Waters ACQUITY UPLC-PDA-ELSD-MS system using a $C_{18}$ reverse phase column and 0.1% formic acid/water—0.1% formic acid/acetonitrile binary solvent system. All synthesized compounds were at least 98% pure. The structures of the synthesized compounds were confirmed by $^1$H NMR and $^{13}$CNMR recorded either on 400 Mhz Varian AVANCE 400-FT NMR or 500 Mhz AVANCE III HD NMR.

Representative Procedure for Synthesis of Nitroimidazole-tetramic Acid Hybrid Molecules Wherein the Nitroimidazole is Linked to the 1N-position of the Tetramic Acid as Depicted in FIG. 1

Synthesis of 3-acetyl-4-hydroxy-5-methyl-1-(2-(2-methyl-5-nitro-1H-imidazol-1-yl)ethyl)-1H-pyrrol-2(5H)-on (2158): 2-nitrobenzene-1-sulfonyl chloride (443 mg, 2 mmol, 1 eq.) were added to an ice cold suspension of Ala-OMe.HCl (307 mg, 2.2 mmol, 1.1 eq.) and triethylamine (613 µl, 4.40 mmol, 2.2 eq.) in 8 ml of dry DCM and maintained under $N_2$. After stirring for 1 h at room temperature the mixture was filtered and the residue rinsed with EtOAc (50 ml). The organic layer was extracted with 5% citric acid, brine, dried over $Na_2SO_4$ and concentrated to provide 518 mg (90% yield) of Nosyl-Ala-OMe as yellow oil that was used in the next step without further purification.

To a cold mixture of Nosyl-Ala-OMe, Triphenylphosphine (613 mg, 2.34 mmol, 1.3 eq.) and metronidazole (308 mg, 1.797 mmol, 1 eq.) in 10 ml of dry THF and under $N_2$ atmosphere were slowly added (E)-diethyl diazene-1,2-dicarboxylate (423 µl, 2.7 mmol, 1.5 eq.) and the mixture stirred overnight at room temperature. The solvent was evaporated and the residue dissolved in 15 ml ACN/DMSO (49:1). To this were added 4-methoxybenzenethiol (1326 µl, 10.78 mmol, 6 eq.) and $K_2CO_3$ (1987 mg, 14.38 mmol, 8 eq.) and the mixture stirred vigorously for 3 h. The mixture was filtered through a celite pad and the residue washed with DCM (30 ml). The solvent was evaporated and the residue dissolved in 25 ml EtOAc. The EtOAc layer was extracted with cold 5% HCl. The cold HCl layer was then basified with 2N NaOH to a pH of 9-10 and extracted with EtOAc (30 ml×3). The EtOAc layer were combined, washed with brine, dried over $Na_2SO_4$ and concentrated to provide 390 mg (1.522 mmol) of the secondary amine methyl 2-((2-(5-methyl-2-nitro-1H-imidazol-1-yl)ethyl)amino)propanoate as oil that was used in the next step without further purification.

To the oil were added 12 ml of dry toluene and 2,2,6-trimethyl-4H-1,3-dioxin-4-one (201 µl, 1.522 mmol, 1 eq.) and the mixture refluxed under $N_2$ for 2 h. The toluene was evaporated and the residue was dissolved in 25 ml of dry MeOH. 900 mg (~2 eq, 3.5 mmol/g) of A-26(OH) resin were added and the mixture stirred overnight at room temperature under $N_2$. The resin was filtered off and washed with MeOH (10 ml×3). The resin was suspended in 20 ml MeOH and 470 µl (~4 eq) TFA were added. After stirring for 30 mins the resin was filtered off and washed with MeOH (10 ml×3). The combined MeOH layers were concentrated and the crude mixture was purified by reverse phase column chromatography to provide 232 mg [overall 38% starting from Ala-OMe. HCl (2 mmol)] of 2158. $^1$H NMR (400 MHz, MeOD) δ 1.30 (d, J=6.96 Hz, 3H), 2.44 (s, 3H), 2.52 (s, 3H), 3.65-3.72 (m, 1H), 3.91-3.99 (m, 2H), 4.55-4.67 (m, 2H), 7.97 (s, 1H). $^{13}$C NMR (126 MHz, CDCl$_3$), tautomers were observed for the tetramic carbons, δ 14.04, 15.27, 19.51 (20.27), 40.17, 44.02, 62.22 (59.29), 76.81, 77.06, 77.32, 100.86 (103.82), 133.39, 138.43, 150.82, 173.47 (167.31), 184.79 (188.70), 193.97 (200.05). ESI-MS: calc. for $C_{13}H_{15}N_4O_5$ [M-H]$^-$: 307.28; found: 307.18.

3-acetyl-4-hydroxy-1-(2-(2-methyl-5-nitro-1H-imidazol-1-yl)ethyl)-1H-pyrrol-2(5H)-one(2153): $^1$H NMR (400 MHz, MeOD) δ 2.42 (s, 3H), 2.49 (s, 3H), 3.84 (t, J=6.0 Hz, 2H), 3.89 (s, 2H), 4.63 (t, J=6.0 Hz, 2H), 7.96 (s, 1H), 8.09 (s, 1H). $^{13}$C NMR (126 MHz, MeOD) δ 12.41, 18.73, 40.97, 43.76, 55.04, 102.44, 131.50, 138.90, 150.88, 171.97, 185.25, 193.02. ESI-MS calc. for $C_{13}H_{15}N_4O_5$ [M-H]$^-$: 293.26; found: 293.18.

3-acetyl-4-hydroxy-5-isopropyl-1-(2-(2-methyl-5-nitro-1H-imidazol-1-yl)ethyl)-1H-pyrrol-2(5H)-one (2156): $^1$H NMR (400 MHz, MeOD) δ 0.83 (d, J=6.9 Hz, 3H), 1.19 (d, J=7.0 Hz, 3H), 2.29 (ddd, J=10.5, 6.8, 3.4 Hz, 1H), 2.43 (s, 3H), 2.54 (s, 3H), 3.55 (dt, J=14.5, 5.8 Hz, 1H), 3.83 (d, J=3.2 Hz, 1H), 4.09 (dt, J=14.7, 7.4 Hz, 1H), 4.61 (dd, J=7.4, 5.8 Hz, 2H), 7.96 (s, 1H). $^{13}$CNMR (126 MHz, CDCl$_3$), tautomers were observed for the tetramic carbons, δ 14.01, 17.86, 29.09, 30.92, 40.04, 43.73, 70.13 (67.36), 102.22 (105.00), 133.30, 138.38, 150.90, 174.12 (168.11), 183.94 (188.75), 193.48 (199.16). ESI-MS: calc. for $C_{15}H_{19}N_4O_5$ [M-H]$^-$: 335.34; found: 334.98.

3-acetyl-5-(sec-butyl)-4-hydroxy-1-(2-(2-methyl-5-nitro-1H-imidazol-1-yl)ethyl)-1H-pyrrol-2(5H)-one (2155): $^1$H NMR (400 MHz, MeOD) δ 0.76 (d, J=6.9 Hz, 3H), 1.02 (t, J=7.4 Hz, 3H), 1.52-1.65 (m, 1H), 1.65-1.78 (m, 1H), 1.92-2.04 (m, 1H), 2.43 (s, 3H), 2.54 (s, 3H), 3.55 (dt, J=14.5, 6.0 Hz, 1H), 3.86 (d, J=3.1 Hz, 1H), 4.06 (dt, J=14.5, 7.3 Hz, 1H), 4.60 (dd, J=7.3, 6.0 Hz, 2H), 7.97 (s, 1H). $^{13}$C NMR (126 MHz, CDCl$_3$), tautomers were observed for the tetramic carbons, δ 12.20, 13.48 (13.10), 14.04, 19.41 (20.59), 25.19 (25.41), 35.82, 39.67 (40.05), 43.78, 65.96, 68.75, 76.80, 77.05, 77.31, 102.36 (105.49), 133.38, 138.40, 150.81 (151.00), 174.09 (168.08), 183.89 (188.73), 193.48 (199.35). ESI-MS: calc. for $C_{16}H_{21}N_4O_5$ [M-H]$^-$: 349.36; found: 349.09.

3-acetyl-4-hydroxy-5-isobutyl-1-(2-(2-methyl-5-nitro-1H-imidazol-1-yl)ethyl)-1H-pyrrol-2(5H)-one (1971): $^1$H NMR (400 MHz, MeOD) δ 0.92 (t, J=6.7 Hz, 6H), 1.55-1.72 (m, 2H), 1.86 (dt, J=13.8, 6.7 Hz, 1H), 2.43 (s, 3H), 2.52 (s, 3H), 3.58 (dt, J=14.6, 5.8 Hz, 1H), 3.87 (br s, 1H), 4.02 (dt, J=14.4, 7.1 Hz, 1H), 4.61 (dd, J=7.1, 5.7 Hz, 2H), 7.97 (s, 1H). $^{13}$C NMR (126 MHz, MeOD) δ 12.37, 18.41, 21.47, 22.37, 23.93, 37.90, 39.24, 43.63, 63.05, 101.92, 131.51, 138.88, 150.98, 171.83, 185.19, 196.35. ESI-MS: calc. for $C_{16}H_{21}N_4O_5$ [M-H]$^-$: 349.36; found: 349.24.

3-acetyl-4-hydroxy-1-(2-(2-methyl-5-nitro-1H-imidazol-1-yl)ethyl)-5-(2-(methylthio)ethyl)-1H-pyrrol-2(5H)-one (2157): $^1$H NMR (400 MHz, MeOD) δ 1.87 (m, 1H), 1.89 (s, 3H), 1.99 (dddd, J=14.6, 9.0, 7.0, 3.4 Hz, 1H), 2.23 (m, 1H), 2.25 (s, 3H), 2.30 (m, 1H), 2.34 (s, 3H), 3.38 (dt, J=14.6, 5.7 Hz, 1H), 3.78-3.96 (m, 2H), 4.43 (dd, J=7.2, 5.7

Hz, 2H), 7.78 (s, 1H). $^{13}$C NMR (101 MHz, MeOD) δ 13.81, 15.29, 19.89, 29.18, 29.42, 40.53, 45.03, 64.65, 103.51, 132.98, 140.29, 152.37, 173.51, 186.44, 196.98. ESI-MS: calc. for $C_{15}H_{19}N_4O_5S$ [M-H]$^-$: 367.40; found: 366.89.

3-acetyl-5-benzyl-4-hydroxy-1-(2-(2-methyl-5-nitro-1H-imidazol-1-yl)ethyl)-1H-pyrrol-2(5H)-one (2154): $^1$H NMR (400 MHz, MeOD) δ 2.29 (s, 3H), 2.49 (s, 3H), 3.07-3.28 (m, 2H), 3.57 (dt, J=14.7, 5.3 Hz, 1H), 4.12 (ddd, J=14.2, 7.7, 6.1 Hz, 1H), 4.24 (t, J=4.6 Hz, 1H), 4.42-4.66 (m, 1H), 7.11-7.28 (m, 5H), 8.09 (s, 1H). $^{13}$C NMR (126 MHz, CDCl$_3$) δ 13.18, 19.64, 35.99, 40.06, 43.94, 66.19, 76.87, 77.12, 77.38, 101.57, 127.42, 128.83, 129.03, 130.72, 134.93, 138.22, 150.14, 174.12, 185.06, 193.01. ESI-MS: calc. for $C_{19}H_{19}N_4O_5$ [M-H]$^-$: 383.34; found: 382.99.

3-acetyl-5-(4-(tert-butoxy) benzyl)-4-hydroxy-1-(2-(2-methyl-5-nitro-1H-imidazol-1-yl)ethyl)-1H-pyrrol-2(5H)-one (2171): $^1$H NMR (400 MHz, MeOD) δ 1.28 (s, 9H), 2.29 (s, 3H), 2.46 (s, 3H), 3.09 (dd, J=14.6, 4.3 Hz, 1H), 3.15-3.26 (m, 1H), 3.55 (dt, J=14.6, 5.4 Hz, 1H), 4.12-4.24 (m, 2H), 4.57 (dd, J=6.7, 5.1 Hz, 2H), 6.81-6.91 (m, 2H), 6.96-7.08 (m, 2H), 7.94 (s, 1H). $^{13}$C NMR (101 MHz, MeOD) δ 13.80, 19.63, 29.18, 35.33, 40.46, 44.91, 66.40, 79.64, 103.74, 125.17, 131.15, 132.97, 140.30, 152.30, 155.68, 173.34, 185.89, 196.76. ESI-MS: calc. for $C_{23}H_{27}N_4O_6$ [M-H]$^-$: 455.48; found: 455.21.

3-acetyl-4-hydroxy-5-(4-hydroxybenzyl)-1-(2-(2-methyl-5-nitro-1H-imidazol-1-yl)ethyl)-1H-pyrrol-2(5H)-one (2172): $^1$H NMR (500 MHz, MeOD) δ 2.33 (s, 3H), 2.45 (s, 3H), 3.05 (dd, J=14.6, 3.5 Hz, 1H), 3.16 (dd, J=14.9, 3.4 Hz, 1H), 3.54 (dd, J=14.4, 6.6 Hz, 1H), 4.11-4.18 (m, 2H), 4.58 (t, J=7.5 Hz, 2H), 6.64 (d, J=7.1 Hz, 2H), 6.90 (d, J=7.6 Hz, 2H), 7.94 (s, 1H). $^{13}$C NMR (126 MHz, CDCl$_3$) δ 13.71, 19.50, 35.19, 40.03, 43.77, 66.62, 101.49, 115.40, 115.69, 130.14, 130.45, 132.88, 138.39, 150.75, 155.91, 163.12, 173.64, 184.41, 193.57. ESI-MS: calc. for $C_{19}H_{19}N_4O_6$ [M-H]$^-$: 399.38; found: 399.20.

5-([1,1'-biphenyl]-4-ylmethyl)-3-acetyl-4-hydroxy-1-(2-(2-methyl-5-nitro-1H-imidazol-1-yl)ethyl)-1H-pyrrol-2 (5H)-one (2345): $^1$H NMR (400 MHz, MeOD) δ 2.34 (s, 3H), 2.42 (s, 3H), 3.16 (dd, J=14.6, 4.6 Hz, 1H), 3.27 (dd, J=14.6, 4.8 Hz, 1H), 3.33 (p, J=1.6 Hz, 1H), 3.54 (dt, J=14.6, 5.5 Hz, 1H), 4.14 (dt, J=14.1, 6.9 Hz, 1H), 4.21 (t, J=4.7 Hz, 1H), 4.55 (dd, J=6.7, 5.3 Hz, 2H), 7.14-7.19 (m, 2H), 7.27-7.33 (m, 1H), 7.36-7.42 (m, 2H), 7.45-7.50 (m, 2H), 7.52-7.57 (m, 2H), 7.93 (s, 1H). $^{13}$C NMR (126 MHz, CDCl$_3$), tautomers were observed for the tetramic carbons, δ 13.92 (13.96), 19.52 (20.02), 35.32 (35.63), 40.08 (40.24), 43.64 (43.69), 66.45 (63.45), 76.78, 101.40 (104.58), 126.98, 127.40, 127.42, 128.78, 129.46 (129.55), 133.35, 133.38, 134.10, 138.37, 140.18, 140.22, 140.37, 150.56 (150.81), 173.76 (167.51), 184.68 (188.18), 192.94 (199.19). ESI-MS: calc. for $C_{25}H_{23}N_4O_5$ [M-H]$^-$: 459.47; found: 459.39.

3-acetyl-5-((benzylthio)methyl)-4-hydroxy-1-(2-(2-methyl-5-nitro-1H-imidazol-1-yl)ethyl)-1H-pyrrol-2(5H)-one (2313): $^1$H NMR (400 MHz, MeOD) δ 2.44 (s, 3H), 2.49 (s, 3H), 2.93-3.11 (m, 2H), 3.36-3.46 (m, 1H), 3.69 (s, 2H), 3.92 (dt, J=14.6, 7.3 Hz, 1H), 4.13 (t, J=3.9 Hz, 1H), 4.45-4.62 (m, 2H), 7.18-7.23 (m, 1H), 7.26-7.32 (m, 4H), 7.96 (s, 1H). $^{13}$C NMR (101 MHz, MeOD) δ 13.85, 19.68, 31.60, 37.84, 40.63, 44.99, 49.47, 65.40, 103.74, 115.69, 128.22, 129.57, 130.14, 132.85, 135.76, 139.45, 140.23, 152.31, 173.89, 185.91, 195.65. ESI-MS: calc. for $C_{20}H_{21}N_4O_5S$ [M-H]$^-$: 429.47; found: 429.04.

3-acetyl-5-(1-(tert-butoxy)ethyl)-4-hydroxy-1-(2-(2-methyl-5-nitro-1H-imidazol-1-yl)ethyl)-1H-pyrrol-2(5H)-one (2173): $^1$H NMR (400 MHz, MeOD) δ 1.16 (s, 9H), 1.28 (dd, J=6.7, 1.0 Hz, 3H), 2.43 (s, 3H), 2.56 (s, 3H), 3.73 (d, J=3.5 Hz, 1H), 3.80-3.91 (m, 1H), 4.01-4.15 (m, 2H), 4.53-4.65 (m, 1H), 4.73 (dt, J=14.2, 6.8 Hz, 1H), 7.97 (s, 1H). $^{13}$C NMR (126 MHz, CDCl$_3$), tautomers were observed for the tetramic carbons, δ 14.09, 19.36 (19.67), 20.46 (21.97), 28.12 (28.31), 42.01 (42.10), 44.05, 66.72 (66.29), 67.99, 71.31, 74.30 (74.76), 101.80 (105.16), 133.21, 138.47, 151.07, 174.28 (168.20), 183.72 (188.42), 192.97 (198.44). ESI-MS: calc. for $C_{18}H_{25}N_4O_6$ [M-H]$^-$: 393.41; found: 393.20.

3-acetyl-4-hydroxy-5-(1-hydroxyethyl)-1-(2-(2-methyl-5-nitro-1H-imidazol-1-yl)ethyl)-1H-pyrrol-2(5H)-one (2174): $^1$H NMR (400 MHz, MeOD) δ 1.35 (d, J=6.5 Hz, 3H), 2.43 (s, 3H), 2.54 (s, 3H), 3.76 (d, J=4.9 Hz, 1H), 3.86 (dt, J=14.5, 5.8 Hz, 1H), 4.01-4.14 (m, 2H), 4.59-4.77 (m, 2H), 7.96 (s, 1H). $^{13}$C NMR (126 MHz, CDCl$_3$) δ 13.88, 19.27, 41.87, 44.19, 67.59, 69.62, 102.27, 132.93, 138.62, 151.04, 174.18, 185.11, 193.70. ESI-MS: calc. for $C_{14}H_{17}N_4O_6$ [M-H]$^-$: 337.31; found: 337.18.

3-acetyl-5-(tert-butoxymethyl)-4-hydroxy-1-(2-(2-methyl-5-nitro-1H-imidazol-1-yl)ethyl)-1H-pyrrol-2(5H)-one (2124): $^1$H NMR (400 MHz, CDCl$_3$) δ 1.19 (s, 9H), 2.49 (s, 3H), 2.70 (s, 3H), 3.65 (dd, J=6.0, 2.5 Hz, 1H), 3.77 (s, 1H), 3.82-3.91 (m, 2H), 3.92-4.03 (m, 1H), 4.59 (dt, J=13.3, 6.2 Hz, 1H), 4.77 (dt, J=12.7, 6.3 Hz, 1H), 8.11 (s, 1H). $^{13}$C NMR (126 MHz, CDCl$_3$) δ 13.73, 19.48, 27.26, 40.72, 44.40, 60.39, 66.81, 74.14, 102.30, 132.18, 138.57, 150.77, 174.08, 184.39, 193.24. ESI-MS: calc. for $C_{17}H_{23}N_4O_6$ [M-H]$^-$: 379.39; found: 378.89.

3-acetyl-4-hydroxy-5-(hydroxymethyl)-1-(2-(2-methyl-5-nitro-1H-imidazol-1-yl)ethyl)-1H-pyrrol-2(5H)-one (2125): $^1$H NMR (500 MHz, CDCl$_3$) δ 2.47 (s, 3H), 2.55 (s, 3H), 3.73 (s, 1H), 3.83 (dd, J=13.5, 6.8 Hz, 2H), 3.92-4.02 (m, 2H), 4.54 (dt, J=13.4, 6.2 Hz, 1H), 4.67 (dt, J=13.5, 6.8 Hz, 1H), 7.97 (s, 1H). $^{13}$C NMR (126 MHz, CDCl$_3$) δ 13.87, 19.53, 40.67, 44.15, 59.81, 68.22, 102.13, 132.91, 138.58, 151.14, 174.08, 184.27, 192.90. ESI-MS: calc. for $C_{13}H_{15}N_4O_6$ [M-H]$^-$: 323.28; found: 323.18.

tert-butyl 3-(4-acetyl-3-hydroxy-1-(2-(2-methyl-5-nitro-1H-imidazol-1-yl)ethyl)-5-oxo-2,5-dihydro-1H-pyrrol-2-yl) propanoate (2175): $^1$H NMR (400 MHz, MeOD) δ 1.44 (s, 9H), 1.97-2.07 (m, 1H), 2.11-2.20 (m, 1H), 2.20-2.27 (m, 2H), 2.44 (s, 3H), 2.52 (s, 3H), 3.58 (ddd, J=14.6, 6.2, 5.0 Hz, 1H), 3.98 (dd, J=6.9, 3.1 Hz, 1H), 4.07 (dt, J=14.5, 7.2 Hz, 1H), 4.58-4.68 (m, 2H), 7.95 (s, 1H). $^{13}$C NMR (101 MHz, MeOD) δ 13.81, 19.87, 25.09, 28.34, 30.32, 40.43, 44.99, 64.58, 81.97, 103.45, 132.92, 140.31, 152.33, 173.50, 186.71, 196.83. ESI-MS: calc. for $C_{19}H_{25}N_4O_7$ [M-H]$^-$: 421.42; found: 421.10.

3-(4-acetyl-3-hydroxy-1-(2-(2-methyl-5-nitro-1H-imidazol-1-yl)ethyl)-5-oxo-2,5-dihydro-1H-pyrrol-2-yl)propanoic acid (2176): $^1$H NMR (400 MHz, MeOD) δ 2.00-2.13 (m, 1H), 2.16-2.29 (m, 1H), 2.29-2.38 (m, 1H), 2.44 (s, 3H), 2.58 (s, 3H), 3.61 (ddd, J=14.7, 6.2, 4.9 Hz, 1H), 4.00-4.16 (m, 2H), 4.57-4.74 (m, 2H), 8.09 (d, J=2.47, 1H). $^{13}$C NMR (126 MHz, CDCl$_3$) δ 13.71, 19.69, 24.22, 28.04, 39.73, 43.90, 63.81, 102.28, 132.55, 138.54, 150.78, 173.06, 174.64, 185.35, 194.35. ESI-MS: calc. for $C_{15}H_{17}N_4O_7$ [M-H]$^-$: 365.32; found: 365.09.

tert-butyl 2-(4-acetyl-3-hydroxy-1-(2-(2-methyl-5-nitro-1H-imidazol-1-yl)ethyl)-5-oxo-2,5-dihydro-1H-pyrrol-2-yl) acetate (2177): $^1$H NMR (400 MHz, MeOD) δ 1.40 (s, 9H), 2.44 (s, 3H), 2.53 (s, 3H), 2.82-2.96 (m, 2H), 3.56 (ddd, J=14.6, 6.4, 5.0 Hz, 1H), 4.03-4.18 (m, 2H), 4.52-4.71 (m, 2H), 7.96 (s, 1H). $^{13}$C NMR (126 MHz, CDCl$_3$) δ 13.99, 19.51, 27.89, 30.91, 35.71, 40.01, 43.86, 62.35, 82.21, 101.39, 133.17, 138.58, 150.62, 168.97, 173.88, 184.37, 192.32. ESI-MS: calc. for $C_{18}H_{23}N_4O_7$ [M-H]$^-$: 407.38; found: 407.20.

2-(4-acetyl-3-hydroxy-1-(2-(2-methyl-5-nitro-1H-imidazol-1-yl)ethyl)-5-oxo-2,5-dihydro-1H-pyrrol-2-yl)acetic acid, TFA (2178): $^1$H NMR (400 MHz, MeOD) δ 2.33 (s, 3H), 2.51 (s, 3H), 2.72 (dd, J=17.6, 5.5 Hz, 1H), 2.86 (dd, J=17.6, 4.0 Hz, 1H), 3.58 (ddd, J=14.8, 6.1, 5.0 Hz, 1H), 3.96 (ddd, J=14.8, 7.5, 6.1 Hz, 1H), 4.08 (dd, J=5.5, 4.0 Hz, 1H), 4.47-4.69 (m, 2H), 8.10 (s, 1H). $^{13}$C NMR (101 MHz, MeOD) δ 13.33, 19.46, 34.84, 40.99, 45.81, 63.06, 103.32, 130.27, 140.22, 151.87, 173.29, 174.09, 185.66, 196.21. ESI-MS: calc. for $C_{14}H_{15}N_4O_7$ [M-H]$^-$: 351.29; found: 351.09.

tert-butyl (4-(4-acetyl-3-hydroxy-1-(2-(2-methyl-5-nitro-1H-imidazol-1-yl)ethyl)-5-oxo-2,5-dihydro-1H-pyrrol-2-yl)butyl)carbamate (2179): $^1$H NMR (400 MHz, MeOD) δ 1.06-1.32 (m, 2H), 1.37-1.53 (m, 12H), 1.89 (dtt, J=14.6, 9.2, 4.3 Hz, 2H), 2.44 (s, 3H), 2.53 (s, 3H), 2.95-3.11 (m, 2H), 3.56 (dt, J=14.5, 5.7 Hz, 1H), 3.97-4.15 (m, 2H), 4.61 (dd, J=7.4, 5.7 Hz, 2H), 7.97 (s, 1H). $^{13}$C NMR (101 MHz, MeOD) δ 12.95, 18.96, 20.24, 27.94, 28.34, 30.01, 39.39, 39.88, 44.07, 64.71, 78.92, 102.84, 132.06, 139.38, 151.44, 157.60, 172.59, 185.46, 196.41. ESI-MS: calc. for $C_{21}H_{30}N_5O_7$ [M-H]$^-$: 464.49; found: 464.21.

3-acetyl-5-(4-aminobutyl)-4-hydroxy-1-(2-(2-methyl-5-nitro-1H-imidazol-1-yl)ethyl)-1H-pyrrol-2(5H)-one, TFA (2180): $^1$H NMR (400 MHz, MeOD) δ 1.08-1.37 (m, 2H), 1.58 (p, J=7.7 Hz, 2H), 1.74-1.98 (m, 2H), 2.33 (s, 3H), 2.54 (s, 3H), 2.83 (t, J=7.6 Hz, 2H), 3.50 (dt, J=14.6, 5.6 Hz, 1H), 3.92-4.07 (m, 2H), 4.50-4.65 (m, 2H), 8.11 (s, 1H). $^{13}$C NMR (101 MHz, MeOD) δ 13.50, 19.89, 21.25, 21.52, 28.42, 29.17, 40.22, 40.44, 45.27, 65.32, 103.59, 131.36, 140.22, 152.08, 173.48, 186.74, 197.11. ESI-MS: calc. for $C_{16}H_{22}N_5O_5$ [M-H]$^-$: 364.36; found: 363.99.

tert-butyl 3-((4-acetyl-3-hydroxy-1-(2-(2-methyl-5-nitro-1H-imidazol-1-yl)ethyl)-5-oxo-2,5-dihydro-1H-pyrrol-2-yl)methyl)-1H-indole-1-carboxylate (2309): $^1$H NMR (400 MHz, MeOD) δ 1.66 (s, 9H), 2.33 (s, 3H), 2.40 (s, 3H), 3.23 (ddd, J=15.7, 4.6, 1.0 Hz, 1H), 3.61 (dt, J=14.6, 5.5 Hz, 1H), 4.08 (ddd, J=14.7, 7.4, 6.2 Hz, 1H), 4.19 (t, J=4.7 Hz, 1H), 4.44-4.59 (m, 2H), 7.21 (ddd, J=8.1, 7.2, 1.1 Hz, 1H), 7.29 (ddd, J=8.4, 7.2, 1.3 Hz, 1H), 7.36 (s, 1H), 7.52 (dt, J=7.8, 1.0 Hz, 1H), 7.78 (s, 1H), 8.02-8.11 (m, 1H). $^{13}$C NMR (101 MHz, MeOD) δ 12.88, 18.92, 24.99, 27.59, 39.90, 44.27, 64.75, 84.24, 102.69, 114.85, 115.33, 119.30, 122.87, 124.51, 124.84, 130.66, 132.01, 135.77, 139.32, 149.97, 151.37, 185.41, 196.01. ESI-MS: calc. for $C_{26}H_{28}N_5O_7$[M-H]$^-$: 522.53; found: 522.13.

5-((1H-indol-3-yl)methyl)-3-acetyl-4-hydroxy-1-(2-(2-methyl-5-nitro-1H-imidazol-1-yl)ethyl)-1H-pyrrol-2(5H)-one (2310): $^1$H NMR (400 MHz, MeOD) δ 2.26 (s, 3H), 2.31 (s, 3H), 3.32-3.41 (m, 2H), 3.46-3.59 (m, 1H), 4.06 (dtd, J=17.8, 6.8, 6.4, 3.4 Hz, 1H), 4.14 (q, J=4.2 Hz, 1H), 4.39-4.51 (m, 2H), 6.92-7.03 (m, 2H), 7.03-7.12 (m, 1H), 7.25-7.35 (m, 1H), 7.43-7.52 (m, 1H), 7.85 (s, 1H). $^{13}$C NMR (101 MHz, MeOD) δ 12.78, 18.89, 25.55, 39.72, 44.23, 65.38, 102.87, 108.23, 111.53, 118.62, 119.10, 121.75, 124.02, 127.73, 132.05, 136.98, 139.36, 151.34, 172.69, 185.10, 196.69. ESI-MS: calc. for $C_{11}H_{20}N_5O_5$[M-H]$^-$: 422.41; found: 422.10.

3-acetyl-4-hydroxy-54(1-methyl-1H-indol-3-yl)methyl)-1-(2-(2-methyl-5-nitro-1H-imidazol-1-yl)ethyl)-1H-pyrrol-2(5H)-one (2490): $^1$H NMR (400 MHz, CDCl$_3$) δ 2.34 (s, 3H), 2.43 (s, 3H), 3.19 (dd, J=15.6, 6.0 Hz, 1H), 3.35 (dd, J=15.6, 4.4 Hz, 1H), 3.48 (dt, J=14.2, 6.0 Hz, 1H), 3.74 (s, 3H), 3.89 (q, J=5.3, 4.8 Hz, 1H), 3.96 (ddd, J=14.4, 7.0, 5.4 Hz, 1H), 4.37-4.43 (m, 2H), 6.77 (s, 1H), 7.10 (ddd, J=8.1, 6.8, 1.2 Hz, 1H), 7.22 (ddd, J=8.1, 6.8, 1.1 Hz, 1H), 7.26-7.30 (m, 1H), 7.49 (d, J=8.0 Hz, 1H), 7.81 (s, 1H). $^{13}$C NMR (101 MHz, CDCl$_3$) δ 0.00, 11.89, 17.60, 24.26, 30.88, 38.10, 42.11, 64.28, 99.56, 106.02, 107.58, 116.69, 117.45, 120.12, 125.46, 125.54, 131.17, 134.98, 136.36, 148.55, 171.89, 182.46, 191.75. ESI-MS: calc. for $C_{22}H_{22}N_5O_5$[M-H]$^-$: 436.44; found: 436.29.

3-acetyl-4-hydroxy-1-(2-(2-methyl-5-nitro-1H-imidazol-1-yl)ethyl)-5-((1-trityl-1H-imidazol-4-yl)methyl)-1H-pyrrol-2(5H)-one (2311): $^1$H NMR (500 MHz, Methanol-d4) δ 2.24 (s, 3H), 2.47 (s, 3H), 3.18 (q, J=15.3 Hz, 2H), 3.42 (dd, J=13.3, 6.0 Hz, 1H), 3.91 (s, 1H), 3.99 (dt, J=13.7, 6.6 Hz, 1H), 4.44 (dd, J=13.9, 6.7 Hz, 1H), 4.48-4.55 (m, 1H), 6.85 (s, 1H), 7.11 (dt, J=6.1, 2.9 Hz, 5H), 7.28 (dt, J=21.6, 7.6 Hz, 1H), 7.41 (q, J=2.9 Hz, 9H), 7.94 (s, 1H), 8.09 (s, 1H). MS-ESI, m/z=615.16 [M-H]$^-$ 5-((1H-imidazol-4-yl)methyl)-3-acetyl-4-hydroxy-1-(2-(2-methyl-5-nitro-1H-imidazol-1-yl)ethyl)-1H-pyrrol-2(5H)-one (2312): $^1$H NMR (400 MHz, MeOD) δ 2.28 (s, 3H), 2.47 (s, 3H), 3.19-3.32 (m, 2H), 3.48 (dt, J=14.6, 5.6 Hz, 1H), 3.92 (dd, J=5.3, 3.9 Hz, 1H), 4.10 (dt, J=14.1, 6.9 Hz, 1H), 4.54 (h, J=8.3, 7.5 Hz, 2H), 7.19 (d, J=1.4 Hz, 1H), 7.91 (s, 1H), 8.11 (s, 1H), 8.67 (d, J=1.4 Hz, 1H). $^{13}$C NMR (126 MHz, MeOD) δ 12.31, 24.31, 39.01, 43.89, 61.62, 101.62, 116.96, 128.52, 131.57, 133.31, 138.83, 150.97, 174.02, 190.91, 193.23. ESI-MS: calc. for $C_{16}H_{17}N_6O_5$ [M-H]$^-$: 373.34; found: 373.09.

3-acetyl-4-hydroxy-1-(2-(2-methyl-5-nitro-1H-imidazol-1-yl)ethyl)-5-(naphthalen-1-ylmethyl)-1H-pyrrol-2(5H)-one (2344): $^1$H NMR (400 MHz, (CD$_3$)$_2$CO) δ 2.28 (s, 3H), 2.36 (s, 3H), 3.43 (dt, J=14.7, 6.0 Hz, 1H), 3.54 (dd, J=14.9, 6.7 Hz, 1H), 3.68 (dd, J=14.9, 5.2 Hz, 1H), 4.09 (dt, J=14.7, 6.4 Hz, 1H), 4.21-4.32 (m, 1H), 4.48 (t, J=6.2 Hz, 2H), 7.39-7.46 (m, 2H), 7.51-7.61 (m, 2H), 7.76 (s, 1H), 7.82-7.86 (m, 1H), 7.92-7.96 (m, 1H), 8.14 (dt, J=8.4, 1.1 Hz, 1H). $^{13}$C NMR (126 MHz, DMSO) δ 13.90, 19.88, 33.09, 43.94, 64.59, 102.09, 124.04, 125.71, 126.15, 126.56, 127.95, 128.31, 129.12, 131.85, 132.74, 133.58, 133.85, 138.77, 151.42, 171.89, 184.10, 194.33. ESI-MS: calc. for $C_{23}H_{21}N_4O_5$[M-H]$^-$: 433.44; found: 433.39.

3-acetyl-4-hydroxy-54(1-methyl-1H-imidazol-4-yl)methyl)-1-(2-(2-methyl-5-nitro-1H-imidazol-1-yl)ethyl)-1H-pyrrol-2(5H)-one (2489): $^1$H NMR (400 MHz, CDCl$_3$) δ 2.39 (s, 3H), 2.52 (s, 3H), 3.13 (dd, J=15.3, 5.0 Hz, 1H), 3.30 (dd, J=15.4, 3.8 Hz, 1H), 3.53 (dd, J=13.9, 6.9 Hz, 1H), 3.80 (s, 3H), 3.86-3.93 (m, 1H), 4.05 (dd, J=14.0, 7.0 Hz, 1H), 4.44-4.49 (m, 2H), 6.78 (s, 1H), 7.94 (s, 1H), 8.13 (s, OH), 8.36 (s, 1H). $^{13}$C NMR (101 MHz, CDCl$_3$) δ 13.95, 23.75, 26.10, 35.11, 39.92, 44.15, 62.56, 102.04, 119.30, 132.10, 133.31, 136.08, 138.42, 151.05, 173.54, 189.39, 192.69. ESI-MS: calc. for $C_{17}H_{19}N_6O_5$[M-H]$^-$: 387.37; found: 387.28.

3-acetyl-4-hydroxy-1-(2-(2-methyl-1H-imidazol-1-yl)ethyl)-5-(naphthalen-1-ylmethyl)-1H-pyrrol-2(5H)-one (2699): $^1$H NMR (400 MHz, MeOD) δ 2.15 (s, 3H), 2.33 (s, 3H), 2.68-2.77 (m, 1H), 3.08 (dd, J=14.6, 9.0 Hz, 1H), 3.65-3.72 (m, 1H), 3.72-3.81 (m, 2H), 3.85-4.01 (m, 2H), 6.84 (d, J=2.0 Hz, 1H), 7.07 (d, J=2.0 Hz, 1H), 7.45 (d, J=7.2 Hz, 2H), 7.53-7.62 (m, 2H), 7.84 (d, J=9.3 Hz, 1H), 7.94 (d, J=7.5 Hz, 1H), 8.22 (d, J=9.1 Hz, 1H). $^{13}$C NMR (126 MHz, DMSO) δ 10.52, 28.67, 34.54, 38.88, 45.55, 62.03, 99.88, 118.33, 122.47, 124.64, 125.82, 126.05, 126.41, 127.33, 127.63, 129.02, 132.25, 133.90, 135.58, 144.09, 174.74, 189.46, 192.83. ESI-MS: calc. for $C_{23}H_{22}N_3O_3$[M-H]$^-$: 388.44; found: 388.33.

5-([1,1'-biphenyl]-4-ylmethyl)-3-acetyl-4-hydroxy-1-(2-(2-methyl-1H-imidazol-1-yl)ethyl)-1H-pyrrol-2(5H)-one (2700): $^1$H NMR (500 MHz, DMSO) δ 2.14 (s, 3H), 2.51 (s, 3H), 3.05 (d, J=13.9 Hz, 1H), 3.19 (d, J=14.7 Hz, 2H), 4.03 (dd, J=22.3, 10.9 Hz, 1H), 4.11 (d, J=13.7 Hz, 2H), 4.15-4.25 (m, 1H), 7.13 (d, J=14.3 Hz, 1H), 7.24 (s, 1H), 7.29 (d, J=7.3 Hz, 2H), 7.33 (d, J=7.0 Hz, 1H), 7.43 (t, J=7.0 Hz, 2H), 7.53 (d, J=7.3 Hz, 2H), 7.64 (d, J=7.1 Hz, 2H). $^{13}$C NMR (126 MHz, DMSO) δ 10.65, 28.17, 34.84, 38.00, 45.58, 61.76, 100.62, 118.26, 118.45, 122.52, 126.60, 126.89, 127.66, 129.32, 130.40, 137.44, 138.29, 140.28, 144.21, 144.31, 174.44, 189.00, 192.67. ESI-MS: calc. for $C_{25}H_{24}N_3O_3$ [M-H]$^-$: 414.48; found: 414.25.

Figure 2:
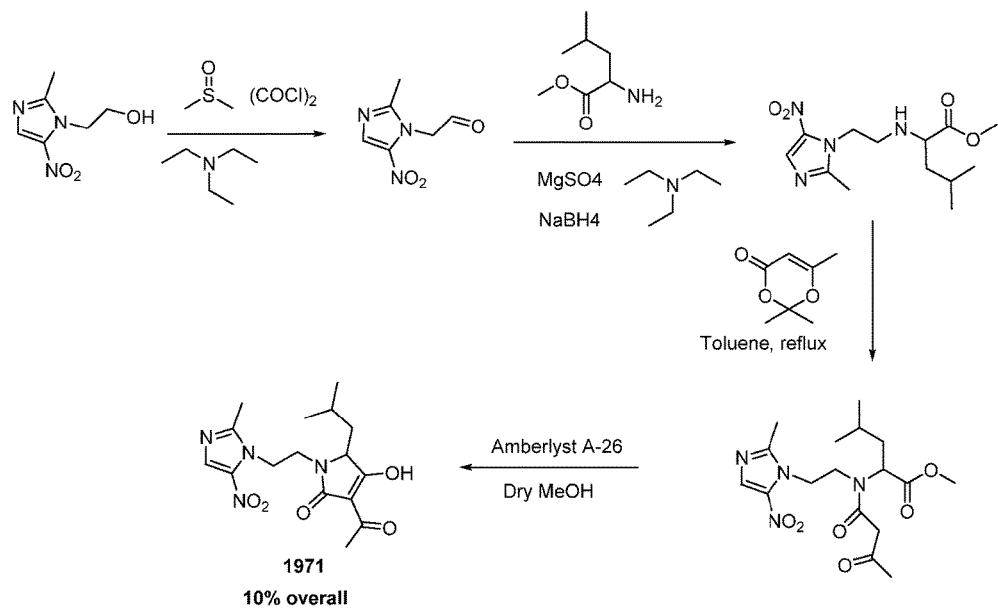
FIG. 2 illustrates an alternate method used for the synthesis of nitroimidazole-tetramic acid hybrid molecules wherein the nitroimidazole is linked to the 1N-position of the tetramic acid derivative.

Alternate Procedure for Preparation of Nitroimidazole-tetramic Acid Hybrid Molecules Wherein the Nitroimidazole is Linked to the 1N-position of the Tetramic Acid as Depicted in FIG. 2

3-acetyl-4-hydroxy-5-isobutyl-1-(2-(2-methyl-5-nitro-1H-imidazol-1-yl)ethyl)-1H-pyrrol-2(5H)-one (1971):

Metronidazole was converted to the aldehyde according to reported methods. A mixture of 2-methyl-5-nitroimidazol-1-yl-acetaldehyde(761 mg, 4.50 mmol), magnesium sulfate (921 mg, 7.65 mmol), Leu-OMe. HCl (817 mg, 4.50 mmol) and triethylamine (627 µl, 4.50 mmol) in 25 ml THF was stirred under $N_2$ for 5 h. The mixture was filtered and the solvent was evaporated in vacuo. The residue was taken up in 20 ml MeOH and treated with sodium borohydride (340 mg, 9.00 mmol). After stirring for 30 mins, 20 ml of aqueous 1N NaOH were added and the reaction mixture extracted with EtOAc (20 ml×3). The EtOAc layers were combined, washed with brine, dried over $Na_2SO_4$ and concentrated. The mixture was purified by column chromatography [Hex/EtOAc (5-100%)] to provide 22% of the desired secondary amine. $^1$H NMR (400 MHz, Chloroform-d) δ 0.80 (d, J=6.6 Hz, 3H), 0.87 (d, J=6.6 Hz, 3H), 1.35-1.38 (m, 1H), 1.49-1.66 (m, 2H), 2.50 (s, 3H), 2.67 (dt, J=13.0, 6.7 Hz, 1H), 3.05-3.16 (m, 2H), 3.69 (s, 3H), 4.35 (t, J=5.8 Hz, 2H), 7.93 (s, 1H). The secondary amine was used in subsequent reactions as described in FIG. 1 and above to afford 1971 in 10% yield (starting from metronidazole).

Figure 3:
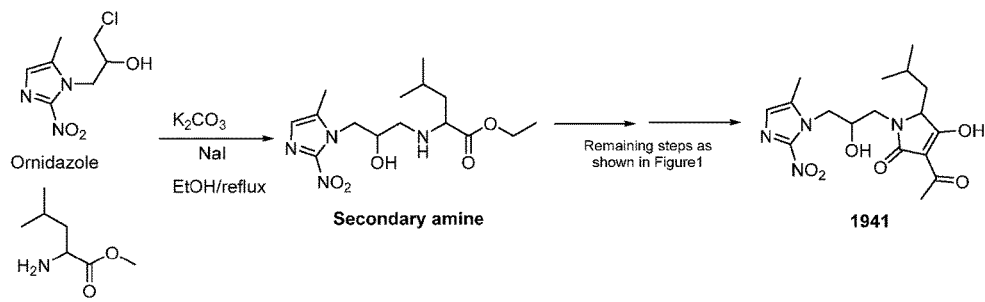
FIG. 3 illustrates a second alternate method used for the synthesis of nitroimidazole-tetramic acid hybrid molecules wherein the nitroimidazole is linked to the 1N-position of the tetramic acid derivative.

Second Alternate Procedure for Preparation of Nitroimidazole-tetramic Acid Hybrid Molecules Wherein the Nitroimidazole is Linked to the 1N-position of the Tetramic Acid as Depicted in FIG. 3

Figure 4:
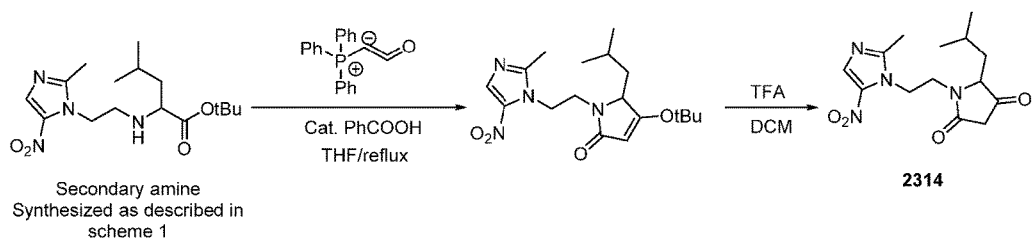
FIG. 4 illustrates an example of the synthesis of a nitroimidazole-tetramic acid hybrid molecule where the 3-position of the tetramic core is unsubstituted (e.g. 2314).

3-acetyl-4-hydroxy-1-(2-hydroxy-3-(5-methyl-2-nitro-1H-imidazol-1-yl)propyl)-5-isobutyl-1H-pyrrol-2(5H)-one (1941): A mixture ornidazole (500 mg, 2.277 mmol), Leu-OMe. HCl (827 mg, 4.55 mmol), $K_2CO_3$ (629 mg, 4.55 mmol) and sodium iodide (34.1 mg, 0.228 mmol) in 15 ml absolute ethanol was refluxed for 24 h. The crude mixture was purified by reverse phase chromatography to provide 520 mg (67%) of the secondary amine methyl 2-((2-hydroxy-3-(5-methyl-2-nitro-1H-imidazol-1-yl)propyl)amino)-4-methylpentanoate. This intermediate was used in subsequent reactions as described in FIG. 1 and above. Purification of the final mixture by reverse phase chromatography afforded 28% of 1941. $^1$H NMR (400 MHz, Methanol-d4) δ 0.93 (dd, J=6.4, 4.1 Hz, 3H), 0.97 (dd, J=6.5, 3.4 Hz, 3H), 1.67-1.81 (m, 2H), 1.81-1.97 (m, 1H), 2.47 (d, J=2.1 Hz, 3H), 2.55 (d, J=9.0 Hz, 3H), 3.33 (p, J=1.7 Hz, 2H), 4.02 (dt, J=14.2, 6.3 Hz, 1H), 4.08-4.27 (m, 3H), 4.54-4.67 (m, 1H), 7.96 (s, 1H). MS-ESI, m/z=379.01 [M-H]$^-$ Representative Procedure for the Synthesis of Nitroimidazole-tetramic Acid Hybrid Molecules where the 3-position of the Tetramic Core is Unsubstituted as Depicted in FIG. 4

Figure 5:
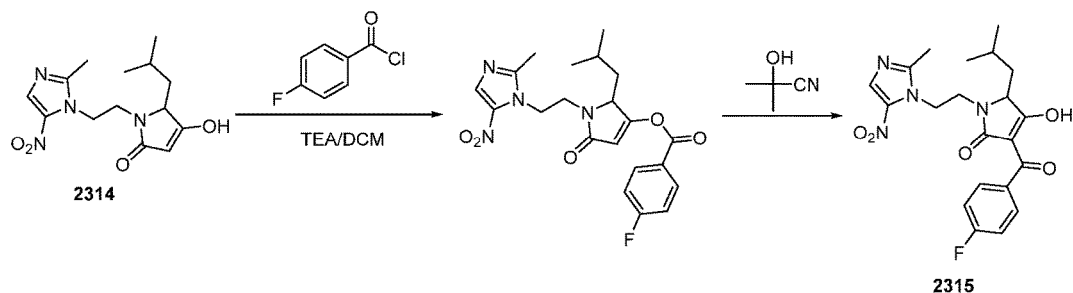
FIG. 5 illustrates an example of introducing acyl substituents at the 3-position of the tetramic core (e.g. 2315).

4-hydroxy-5-isobutyl-1-(2-(2-methyl-5-nitro-1H-imidazol-1-yl)ethyl)-1H-pyrrol-2(5H)-one, TFA (2314): Under $N_2$ atmosphere, a mixture of tert-butyl 4-methyl-24(2-(2-methyl-5-nitro-1H-imidazol-1-yl)ethyl)amino)pentanoate (873 mg, 2.56 mmol), (Triphenylphosphoranylidene)ketene (775 mg, 2.56 mmol) and benzoic acid (62.6 mg, 0.513 mmol) in 10 ml dry THF was stirred at 65° C. for 16 h. The solvent was evaporated and the crude purified by column (Hex/EtOAc/MeOH) to provide 393 mg (42%) of 4-(tert-butoxy)-5-isobutyl-1-(2-(2-methyl-5-nitro-1H-imidazol-1-yl)ethyl)-1H-pyrrol-2(5H)-one. To this were added 10 ml of TFA/DCM (1:1) and the mixture stirred for 1 h. The solvent was evaporated and the residue purified by reverse column phase chromatography to provide 42% of 2314 as yellow oil. $^1$H NMR (400 MHz, Chloroform-d) δ 0.93 (t, J=6.9 Hz, 6H), 1.53-1.65 (m, 2H), 1.78-1.90 (m, 2H), 2.58 (s, 3H), 3.02 (d, J=22.3 Hz, 1H), 3.12 (d, J=22.3 Hz, 1H), 3.82-3.93 (m, 2H), 4.51-4.61 (m, 2H), 7.98 (s, 1H). MS-ESI, m/z=307.12 [M-H]$^-$ Representative Procedure for Acylating the Unsubstituted 3-position of Nitroimidazole-tetramic Acid Hybrid Molecules Wherein the Nitroimidazole is Linked to the 1N-position of the Tetramic Acid as Depicted in FIG. 5

Figure 6:
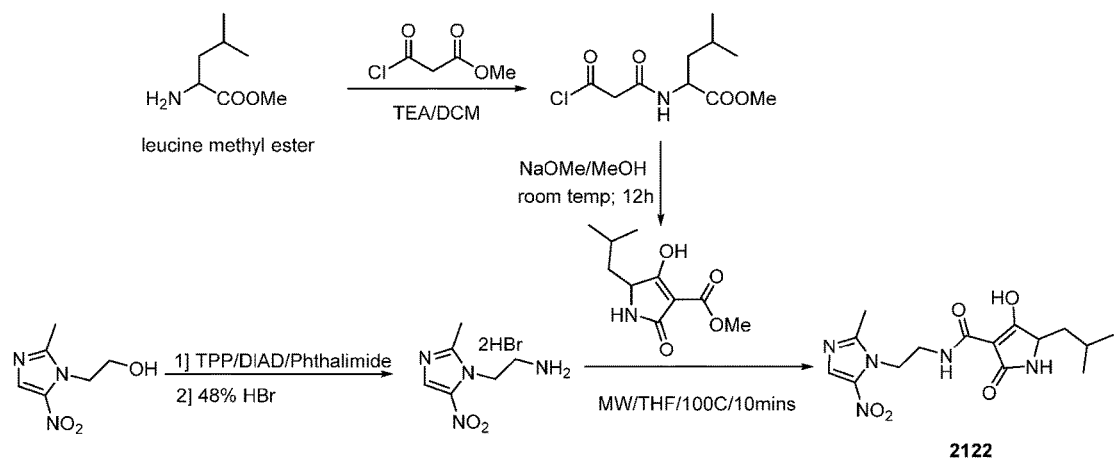
FIG. 6 illustrates an example of the synthesis of a nitroimidazole-tetramic acid hybrid molecule in which the nitroimidazole is attached to the 3-position of the tetramic acid derivative via a carboxamide (X is —CONH—).

(R)-3-(4-fluorobenzoyl)-4-hydroxy-5-isobutyl-1-(2-(2-methyl-5-nitro-1H-imidazol-1-yl)ethyl)-1H-pyrrol-2(5H)-one (2315): To an ice cold solution of (R)-4-hydroxy-5-isobutyl-1-(2-(2-methyl-5-nitro-1H-imidazol-1-yl)ethyl)-1H-pyrrol-2(5H)-one, TFA i.e. 2314 (400 mg, 0.947 mmol) and triethylamine (554 µl, 3.98 mmol) in 12 ml of dry DCM were added 4-fluorobenzoyl chloride (112 µl, 0.947 mmol). After stirring for 45 mins, acetone cyanohydrin (87 µl, 0.947 mmol) was added and the mixture stirred at room temperature for 12 h. The solvent was evaporated and the crude purified by reverse phase column chromatography to afford 36% of title compound. $^1$H NMR (400 MHz, Methanol-d4) δ 0.94 (dd, J=8.3, 6.5 Hz, 6H), 1.64-1.80 (m, 2H), 1.82-1.94 (m, 1H), 2.54 (s, 3H), 3.64 (dt, J=14.5, 5.8 Hz, 1H), 3.97 (dd, J=7.1, 4.1 Hz, 1H), 4.07 (dt, J=14.5, 7.2 Hz, 1H), 4.58-4.71 (m, 2H), 7.24 (t, J=8.8 Hz, 2H), 7.98 (s, 1H), 8.21-8.30 (m, 2H). MS-ESI, m/z=429.14 [M-H]$^-$ Representative Procedure for Synthesis of Nitroimidazole-tetramic Acid Hybrid Molecules in which the Nitroimidazole is Attached to the 3-position of the Tetramic Acid where X is —CONH— as Depicted in FIG. 6

4-hydroxy-5-isobutyl-N-(2-(5-methyl-2-nitro-1H-imidazol-1-yl)ethyl)-2-oxo-2,5-dihydro-1H-pyrrole-3-carboxamide (2122): The intermediates for synthesis of 2122 were prepared as follows—the alcohol of metronidazole was converted to the amine, 2-(5-methyl-2-nitro-1H-imidazol-1-yl)ethanamine 2HBr, by first reacting with pthalamide under Mitsunobu conditions using triphenylphosphine (TPP) and Diisopropyl azodicarboxylate (DIAD) followed by deprotection of the amine using 48% HBr. The 3-methoxycarbonyl tetramic acid was synthesized from Leu-OMe hydrochloric acid and methyl malonyl chloride using Lacey-Dieckmann conditions.

For synthesis of 2122, a mixture of the 3-methoxycarbonyl tetramic acid (156 mg, 0.732 mmol), 2-(5-methyl-2-nitro-1H-imidazol-1-yl)ethanamine 2HBr (243 mg, 0.732 mmol) and triethylamine (306 µl, 2.196 mmol) in 5 ml THF were heated in microwave at 100° C. for 5 mins. The crude mixture was purified by reverse phase column chromatography to afford 39% product. $^1$H NMR (400 MHz, MeOD) δ 0.98 (dd, J=6.6, 3.8 Hz, 6H), 1.43 (ddd, J=14.0, 9.1, 5.2 Hz, 1H), 1.66 (ddd, J=13.4, 9.0, 4.2 Hz, 1H), 1.78-1.89 (m, 1H), 2.47 (s, 3H), 3.79 (dd, J=6.3, 5.1 Hz, 2H), 4.12 (dd, J=9.1, 4.2 Hz, 1H), 4.57 (dd, J=6.3, 5.0 Hz, 2H), 7.92 (s, 1H). $^{13}$C NMR (126 MHz, MeOD) δ 12.52, 20.75, 22.39, 24.70, 37.07, 40.55, 45.62, 56.18, 131.19, 139.00, 151.03, 166.29, 172.44, 187.94. ESI-MS: calc. for $C_{15}H_{20}N_5O_5$ [M-H]$^-$: 350.35; found: 350.09.

Figure 7:
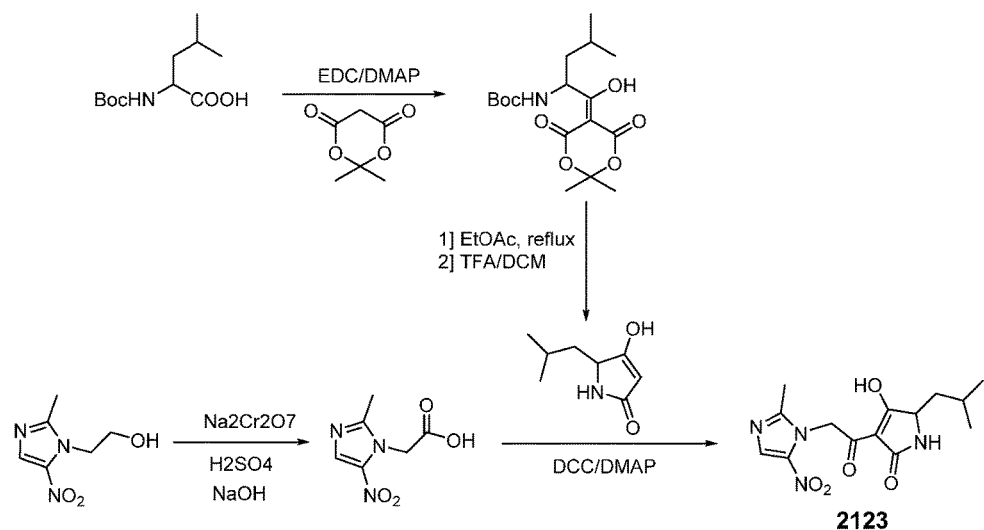
FIG. 7 illustrates an example of the synthesis of a nitroimidazole-tetramic acid hybrid molecule in which the nitroimidazole is attached to the 3-position of the tetramic acid derivative via a carboxyl group (X is —CO—).

Representative Procedure for Synthesis of Nitroimidazole-tetramic Acid Hybrid Molecules in which the Nitroimidazole is Attached to the 3-position of the Tetramic Acid where X is —CO— as Depicted in FIG. 7

4-hydroxy-5-isobutyl-3-(2-(2-methyl-5-nitro-1H-imidazol-1-yl)acetyl)-1H-pyrrol-2(5H)-one (2123)

The intermediates for synthesis of 2123 were prepared as follows—the alcohol of metronidazole was oxidized to acid, 2-(2-methyl-5-nitro-1H-imidazol-1-yl)acetic acid, by Jones oxidation using sodium dichromate and sulfuric acid. The tetramic acid, 4-hydroxy-5-isobutyl-1H-pyrrol-2(5H)-one, was synthesized from Z-Leu-OH and (Triphenylphosphoranylidene)ketene which afforded the benzyl protected tetramic acid which was then deprotected by catalytic hydrogenation.

For the synthesis of 2123, a cold mixture of 2-(2-methyl-5-nitro-1H-imidazol-1-yl)acetic acid (337 mg, 1.823 mmol), 4-hydroxy-5-isobutyl-1H-pyrrol-2(5H)-one (246 mg, 1.585 mmol) and 4-dimethylaminopyridine (DMAP) (261 mg, 2.140 mmol) in 10 ml of dry DCM were treated with 1-Ethyl-3-(3-dimethylaminopropyl)carbodiimide (EDC) (376 mg, 1.823 mmol). After stirring at room temperature for 24 h, the crude was purified by reverse phase column chromatography to afford 58% product. $^1$H NMR (400 MHz, MeOD) δ 1.02 (dd, J=6.6, 2.7 Hz, 6H), 1.52 (ddd, J=14.1, 9.5, 4.9 Hz, 1H), 1.72 (ddd, J=13.4, 9.3, 4.0 Hz, 1H), 1.82-1.93 (m, 1H), 2.44 (s, 3H), 4.03 (dd, J=9.5, 3.9 Hz, 1H), 5.66 (s, 2H), 8.00 (s, 1H). $^{13}$C NMR (126 MHz, MeOD) δ 12.02, 20.58, 22.53, 24.77, 40.69, 52.07, 59.55, 106.73, 129.46, 139.04, 151.05, 175.43, 186.14, 194.21. ESI-MS: calc. for $C_{14}H_{17}N_4O_5$ [M-H]$^-$: 321.31; found: 321.18.

Testing

In Vitro Anti-bacterial Testing

The synthesized compounds were initially tested against four virulent *C. difficile* strains: CD1803 (toxinotype III, 95 NAP1), CD1875 (toxinotype V, NAP7), R20291 (ribotype 027—from A. Sonenshein, Tufts University, USA), and BAA-1875 (ribotype 078, from American Type Culture Collection-ATCC). The activities (i.e. Minimum Inhibitory Concentrations-MICs) of test compounds were determined in 24 or 96 well microtitre plates using bacterial inocula of $10^6$ cfu/mL and were defined as the lowest concentration of test compound that inhibited visible growth after 24 h of incubation at 37° C. in an A35 anaerobic chamber (Don-Whitley).

Spectrum of Activity and Mode of Action

A range of clinical isolates of *C. difficile* and representative gut flora bacteria were tested for their susceptibility to metronidazole and test compounds 1971, 2344, 2345, and 2490 by agar dilution in Wilkins-Chalgren agar; activities against metronidazole-resistant *C. difficile* in Brucella agar containing haemin (5 mg/L), vitamin K1 (1 mg/L) and sheep blood (5%). These results are described in FIG. 12 (*C. difficile* isolates) and FIG. 13 (GI microorganisms). The results show that the compounds are as active as metronidazole against several strains of *C. difficile*. The compounds were similarly active against different organisms found in the gastrointestinal tract.

To further validate that the mode of action of compounds is similar to metronidazole, since the activity of metronidazole is attributed to its nitro group, we synthesized and tested the des-nitro analogs 2699 and 2700 of 2344 and 2345, respectively. As shown in FIG. 11, the des-nitro analogs were completely inactive (MIC>128 mg/L) suggesting that the hybrids displayed the same mode of action as metronidazole, involving biochemical reduction of its nitro group to reactive species, which cause cellular damage. Indeed, like metronidazole the hybrids imposed similar cellular stresses in *C. difficile*, which was evident from the upregulation of thioredoxin related genes (trxA1/trxB1 and CDR20291_2024), recA mediated DNA repair and the hybrid cluster protein that responds to nitrosative stress and protein damage. Accordingly, the hybrids were inactive against several *C. difficile* clinical strains displaying stable resistance to metronidazole. These findings indicate that the improved activity of these hybrids over metronidazole is related to their retention in the GI tract, as opposed to an alternate antibacterial mechanism of action.

Caco-2 Cell Permeability Assay

Figure 16:
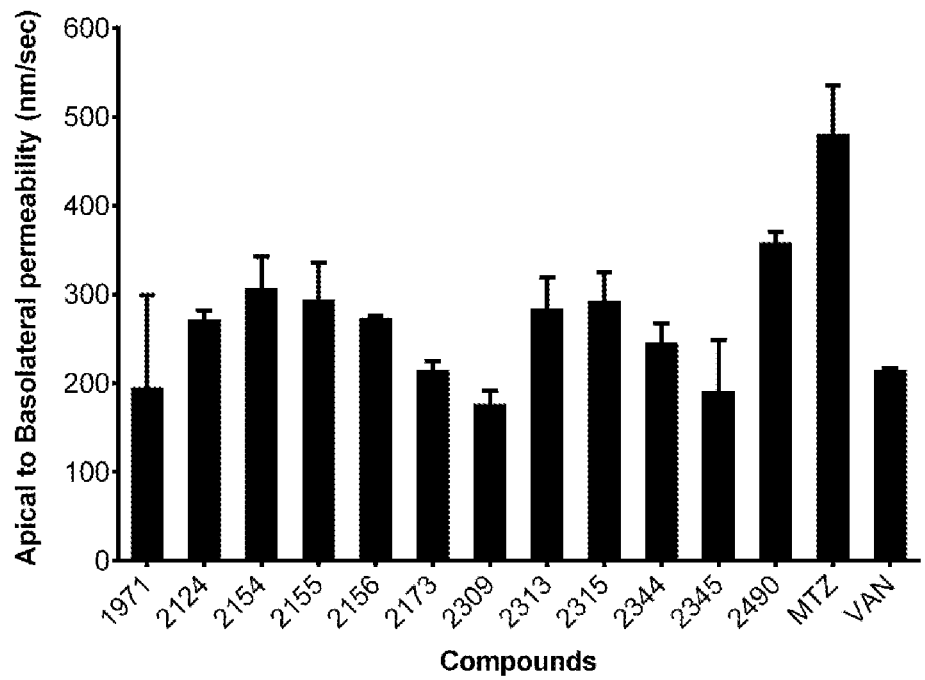
FIG. 16 illustrates the gastrointestinal absorption of compounds from the apical to basolateral side of the Caco-2 monolayer.

To rapidly evaluate whether metronidazole-tetramic acid hybrids displayed poor absorption from the apical side of the gastrointestinal tract, we deployed the Caco-2 cell permeability assay that provides good prediction of compound intestinal absorption. The results are shown in FIG. 15. The permeability co-efficient ($P_{app}$ A-B) of the compounds were calculated and the ability of compounds to move from the apical to the basolateral side of Caco-2 monolayer is shown in FIG. 16.

In accordance with the literature, metronidazole, which is highly absorbed from the GI tract was highly permeable in the assay while vancomycin, which is poorly absorbed (<10%) from the GI tract, displayed poor permeation properties. In contrast to metronidazole, all tetramic acid hybrids (range 176.9±14.3 to 358.5±12 nm/s) displayed poorer permeation from the apical to the basolateral side of cells, implying they are likely to be compartmentalized in the lumen of the gastrointestinal tract. Compounds 2154, 2155, 2313 and 2315 (range 284.5±34.7 to 307±35.6 nm/s) were slightly more permeable than vancomycin, suggesting that within the compound panel there are derivatives that may have some limited permeability, which could be suitable for treating infections residing in intracellular niches.

Efficacy and Pharmacokinetic Studies in Hamsters

Four compounds showing good activity, decreased permeability and which covered a diverse array of substitutions at the 5-position of the tetramic core (1971—isobutyl, 2345—biphenyl, 2344—napthyl and 2490—n-methyl indole) were compared to metronidazole and tested for their efficacy in the hamster model of CDI.

Golden Syrian hamsters (~100 g) from Charles River Laboratories were separately housed in sterile cages and maintained on sterile food and water. On day −1, animals were subcutaneously injected with clindamycin phosphate solution (50 mg/kg, from Hospira). After 20 h (day 0), hamsters were infected by oral gavage with 106 cfu of the *C. difficile* strain ATCC 43596 grown in Sporulation Medium and washed once with pre-reduced PBS; 15. ATCC 43596 is a metronidazole susceptible toxigenic strain that is highly virulent in the hamster model of CDI. During the subsequent days from days 1 to 5 hamsters (n>8 per group) were treated once daily with vehicle (PEG-400: water; 85:15) or 50 mg/kg of test compounds or metronidazole in vehicle. After 5 days of treatment, surviving hamsters were monitored for up to 30 days for signs of disease as described by Anton et al. All moribund animals were euthanized, as well as those that survived the post-treatment monitoring period (30 days); ceca were recovered from all animals. All animal experiments were approved by The Institutional Animal Care and Use Committee of The University of Texas at Arlington.

Pharmacokinetic studies were assessed in male Syrian hamsters (~100 g), from Charles-River, with each carrying a pre-implanted jugular vein cannula. Hamsters (n=5 per group) were fasted overnight and for the duration of the experiment (7 h). After collecting pre-dose blood samples (200 μL), animals were dosed with 100 mg/kg of compounds formulated in PEG-400:water (85:15). At various time points blood samples were collected into heparinized coated tubes that were centrifuged at 3000 rpm for 10 min to yield plasma, which was stored at −20° C.

After dosing animals (n=3 per time point) as above, animals were humanely sacrificed at time points and their cecal contents collected and stored at −20° C. For plasma samples, 25 μL of plasma was placed in 384-well analytical plate and quenched by the addition of 50 μL of acetonitrile containing 4 mg/L warfarin as an internal standard. The plate was sealed, shaken at 600 rpm for 10 min, and then was centrifuged at 4000 rpm for 20 min. 15 μL of the supernatant was transferred to a new analytical 96-well plate and mixed with 100 μL of MilliQ water. The samples were analyzed by injecting 5 μL onto a Waters UPLC/SQD LC-MS/MS system. The cecal samples were processed by adding 100 μL of acetonitrile containing 4 mg/L of warfarin (internal standard) to the microfuge tubes containing cecal matter (~50 mg). The suspension was vortexed for 10 sec, sonicated for 1 min and then centrifuged at 10,000 rpm for 10 min. Aliquots (50 μL) of the collected supernatants were then transferred to a 384-well plate and analyzed by high resolution mass spectroscopy using Waters XEVO QTOF LCMS.

Figure 17:
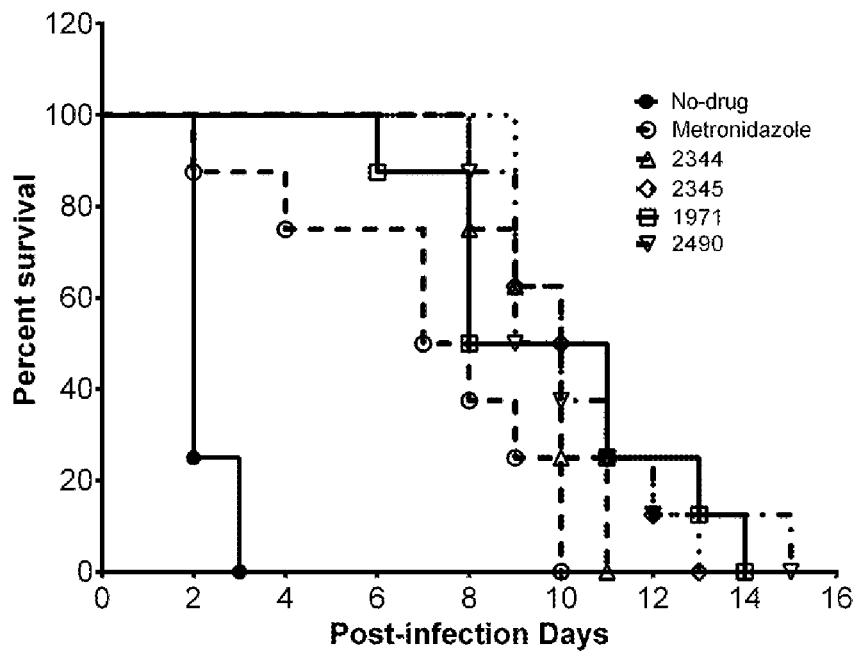
FIG. 17 illustrates the efficacy of metronidazole compared to metronidazole-tetramic acid hybrid compounds in hamster studies.

Efficacy results are shown in FIG. 17. All compounds were well tolerated, with animals showing no signs of adverse effects and statistically (P<0.05) superior to metronidazole in treating an acute form of CDI in hamsters. Animals treated with metronidazole survived a maximum of 10 days post-infection, whilst treatment with the hybrids improved their survival by an additional 1 to 5 days. However, the compounds did not provide complete survival for more than 20 days post-treatment, unlike vancomycin (20 mg/kg). The differences in efficacies between metronidazole and the hybrids were not due to improved activities compared to metronidazole against infecting strain ATCC 43596 as their MICs were similar: 0.125 mg/L for metronidazole, 0.50 mg/L for 1971 and 0.25 mg/L for 2344, 2345 and 2490.

Figure 18:
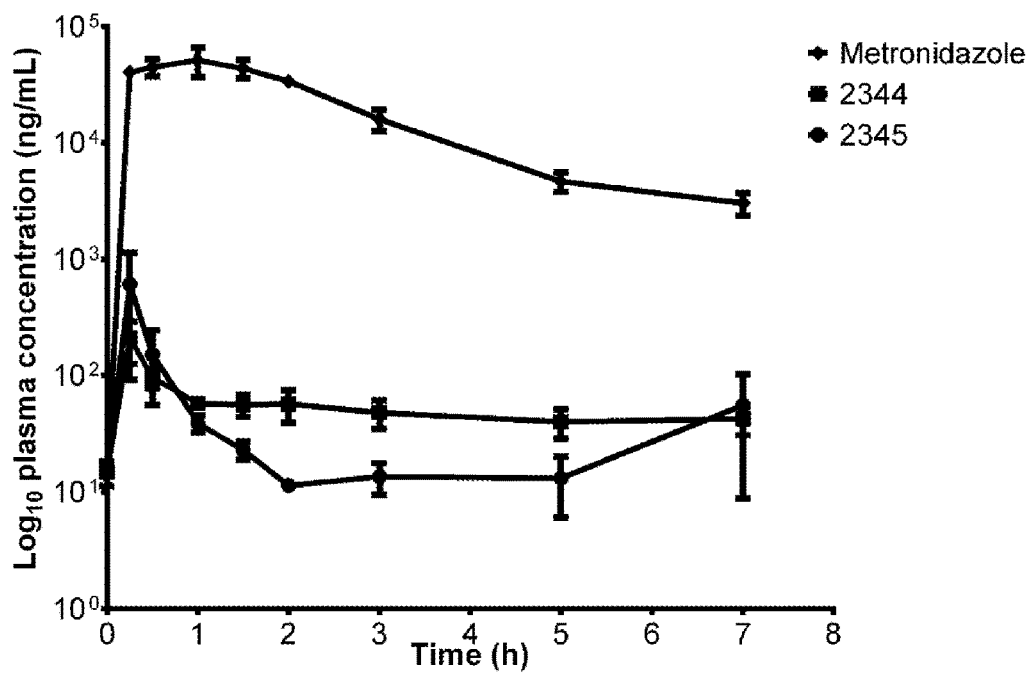
FIG. 18 illustrates peak plasma concentrations for the compounds metronidazole, 2344, and 2345.

In order to test whether the hybrids exhibited poorer permeabilities than metronidazole across the GI tract, we determined the concentrations of 2344, 2345 and metronidazole in the plasma. As seen in FIG. 18, the concentrations of the hybrids in plasma were much lower than metronidazole for both maximum concentration obtained (Cmax (ng/mL): metronidazole, 51,036; 2344, 211; 2345, 616) and total exposure (AUC (h*ng/mL): metronidazole 135,292; 2344, 386; 2345, 355). The Tmax for 2344 and 2345 was 0.25 h and for metronidazole was 1 h.

In vitro ADME assays showed the compounds to be highly stable (t½>4.5 h) in plasma, with much higher serum protein binding than metronidazole, and varying microsomal stability (t½: 2344, 0.30 h; 2345, 1.33 h) (data not shown). Thus, the very low concentration of the hybrids in the plasma might likely be due to a combination of poor intestinal absorption and hepatic clearance.

Figure 19:
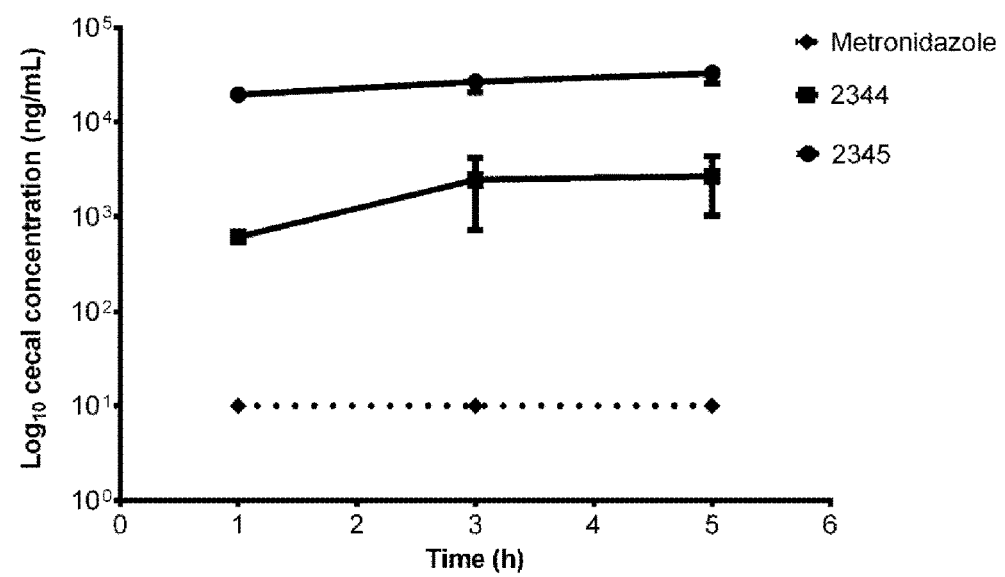
FIG. 19 illustrates peak cecal concentrations for the compounds 2345, 2344, and metronidazole.

To evaluate this in vivo, we determined the concentrations of the three compounds in the cecal contents recovered from hamsters at 1, 3 and 5 h time points following oral dosing (FIG. 19). The mean peak cecal concentrations of 2345 and 2344 were 32,649 ng/mL and 2,678 ng/mL respectively while metronidazole was not detected even at 10 ng/mL (LLOQ for assay). Thus, these hybrids had better retention in the GI tract than metronidazole, which mimics the results from our Caco-2 cell permeability study. The 12-fold difference in the cecal concentration of 2344 and 2345 may reflect better solubility for 2345 in the PEG:water vehicle used (data not shown), since they both possess similar gastric stability profiles; and were also similar in their plasma stability and aqueous solubility at different pHs.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A nitroimidazole-tetramic acid hybrid molecule in which the nitroimidazole is linked to the 1N-position of the tetramic acid and has the formula shown below as Formula I:

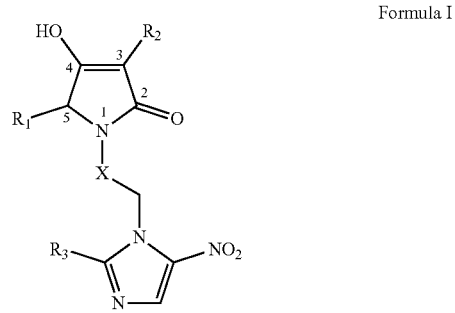

Formula I

Wherein:
A) X is —CH$_2$—, —CH$_2$CH$_2$—, or —C(O)—;
B) R1 is
   i) a straight or branched alkyl chain of one to six carbons,
   ii) a straight or branched alkyl chain of one to four carbons containing a protected polar functional group,
   iii) an optionally substituted saturated or unsaturated, monocyclic or bicyclic ring system of 3 to 16 carbons,
   iv) an aryl alkyl ring system, or
   v) an optionally substituted aryl, biaryl, heteroaryl, or bihetero aryl ring system;
C) R2 is
   i) —C(O)C1-C8 alkyl
   ii) —C(O)-optionally substituted aryl ring, or
   iii) —C(O)-optionally substituted heteroaryl ring system; and
D) R3 is
   i) a hydrogen,
   ii) a straight alkyl chain of one to three carbons, or
   iii) a branched alkyl chain of three to six carbons.

2. The nitroimidazole-tetramic acid hybrid molecule of claim 1, wherein R2 is i) acetyl, propionyl, or butanoyl, ii) benzoyl optionally substituted with chloro, fluoro, bromo, hydroxyl, methyl, ethyl, trifluoromethoxy, or methoxy, or iii) furanoyl, imidazoyl, pyrrodyl, or indaloyl, optionally substituted with chloro, fluoro, bromo, hydroxyl, methyl, ethyl, or methoxy.

3. The nitroimidazole-tetramic acid hybrid molecule of claim 2, wherein R2 is acetyl.

4. The nitroimidazole-tetramic acid hybrid molecule of claim 1, wherein R3 is methyl.

5. The nitroimidazole-tetramic acid hybrid molecule of claim 1, wherein R2 is acetyl, R3 is methyl, and X is —CH2-.

6. The nitroimidazole-tetramic acid hybrid molecule of claim 5, wherein R1 is methyl, ethyl, n-propyl, n-pentyl, n-hexyl, iso-propyl, iso-butyl, sec-butyl, tert-butyl, isopentyl; or R1 is cyclopropyl, cyclobutyl, cyclopentyl, cyclobutyl methyl, cyclopentyl methyl, 1-napthyl, or 2-napthyl optionally substituted with chloro, fluoro, bromo, or methoxy.

7. The nitroimidazole-tetramic acid hybrid molecule of claim 5, wherein R1 is a straight or branched alkyl chain of one to 4 carbon atoms containing hydroxyl, carboxylic acid, amine or thiol group protected with a tert-butyl, benzyl, tert-butyl carbamate or trityl group.

8. The nitroimidazole -tetramic acid hybrid molecule of claim 5, wherein R1 is a branched alkyl chain of three to six carbons.

9. The nitroimidazole-tetramic acid hybrid molecule of claim 5, wherein R1 is isobutyl.

10. The nitroimidazole-tetramic acid hybrid molecule of claim 1, wherein R1 is phenyl or benzyl, optionally substituted with chloro, fluoro, bromo, hydroxyl, methyl, ethyl, methoxy, trifluoromethoxy, morpholinyl, phenyl or piperazinyl.

11. The nitroimidazole-tetramic acid hybrid molecule of claim 1, wherein R1 is benzyl, biphenyl, imidazolyl, pyrrolyl, pyradinyl, pyrazinyl, indolyl, furanyl, thienyl, imidazoyl methyl, pyrrolyl methyl, pyridinyl methyl, pyrazinyl methyl, furanyl methyl, indolyl methyl or thienyl methyl optionally substituted with chloro, fluoro, bromo, hydroxyl, or methoxy.

12. The nitroimidazole-tetramic acid hybrid molecule of claim 1, wherein R3 is ethyl, propyl, iso-propyl, iso-butyl, sec-butyl, tert-butyl or isopentyl.

* * * * *